United States Patent
Yu et al.

(10) Patent No.: US 9,447,193 B2
(45) Date of Patent: Sep. 20, 2016

(54) METHODS FOR SUPPRESSING CANCER BY INHIBITION OF TMCC3

(71) Applicants: Development Center for Biotechnology, New Taipei (TW); Academia Sinica, Taipei (TW); Chang Gung Memorial Hospital, Taoyuan County (TW)

(72) Inventors: Alice L. Yu, New Taipei (TW); John Yu, New Taipei (TW); Ya-Hui Wang, New Taipei (TW); Chuan-Lung Hsu, New Taipei (TW); Yi-Chang Chen, New Taipei (TW); Ying-Yung Lok, New Taipei (TW)

(73) Assignees: Development Center for Biotechnology, New Taipei (TW); Academia Sinica, Taipei (TW); Chang Gung Memorial Hospital, Taoyuan County (TW)

( * ) Notice: Subject to any disclaimer, the term of this patent is extended or adjusted under 35 U.S.C. 154(b) by 0 days.

(21) Appl. No.: 14/223,800

(22) Filed: Mar. 24, 2014

(65) Prior Publication Data
US 2014/0363372 A1 Dec. 11, 2014

Related U.S. Application Data

(60) Provisional application No. 61/804,751, filed on Mar. 24, 2013.

(51) Int. Cl.
*A61K 39/395* (2006.01)
*C07K 16/30* (2006.01)
*G01N 33/574* (2006.01)
*C12Q 1/68* (2006.01)

(52) U.S. Cl.
CPC ..... *C07K 16/3015* (2013.01); *A61K 39/39558* (2013.01); *C07K 16/30* (2013.01); *C12Q 1/6886* (2013.01); *G01N 33/57496* (2013.01); *C07K 2317/55* (2013.01); *C07K 2317/622* (2013.01); *C07K 2317/732* (2013.01); *C07K 2317/734* (2013.01); *C07K 2317/92* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,869,045 A * | 2/1999 | Hellstrom | G01N 33/57484 424/130.1 |
| 2009/0012024 A1* | 1/2009 | Collins | C12Q 1/6886 514/44 R |
| 2011/0020221 A1* | 1/2011 | Berman | A61K 47/48569 424/1.49 |
| 2011/0119776 A1 | 5/2011 | Wong et al. | |
| 2013/0142875 A1 | 6/2013 | Shemi et al. | |
| 2014/0363372 A1 | 12/2014 | Yu et al. | |

FOREIGN PATENT DOCUMENTS

| WO | WO 03/045321 | * | 6/2003 |
|---|---|---|---|
| WO | 2012/031008 A2 | | 3/2012 |

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Wang, Ya-Hui, et al., "Abstract 3317: The roles of TMCC3 in breast cancer cells"; 2012 American Association for Cancer Research 103rd Annual Meeting—Mar. 31-Apr. 4, 2012, Chicago, IL; Cancer Research/aacrjournals.org, Apr. 15, 2012; doi: 10.1158/1538-7445. AM2012-3317 (abstract only) (2 pages).
PCT International Search Report and Written Opinion mailed Mar. 30, 2015, in corresponding International Application No. PCT/US2014/062649 (11 pages).

* cited by examiner

*Primary Examiner* — Mark Halvorson
(74) *Attorney, Agent, or Firm* — Osha Liang LLP

(57) ABSTRACT

A method for treating cancer includes administering to a subject in need thereof an antibody against a transmembrane and coiled-coil domains protein 3 (TMCC3), wherein the antibody binds to an epitope in an extracellular domain of TMCC3. The antibody binds to an epitope in an intercoil domain of TMCC3. A method of diagnosing or assessing a cancer condition includes assessing a level of expression or activity of a transmembrane and coiled-coil domains protein 3 (TMCC3) in a sample, wherein an increase in the level of expression of activity of TMCC3 as compared to a standard indicates the presence of cancer stem cells in the sample.

7 Claims, 28 Drawing Sheets

Figure 1
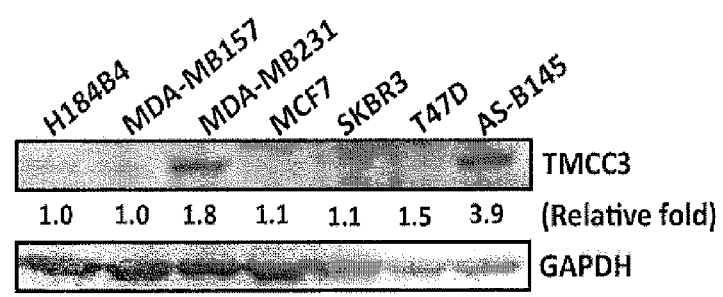
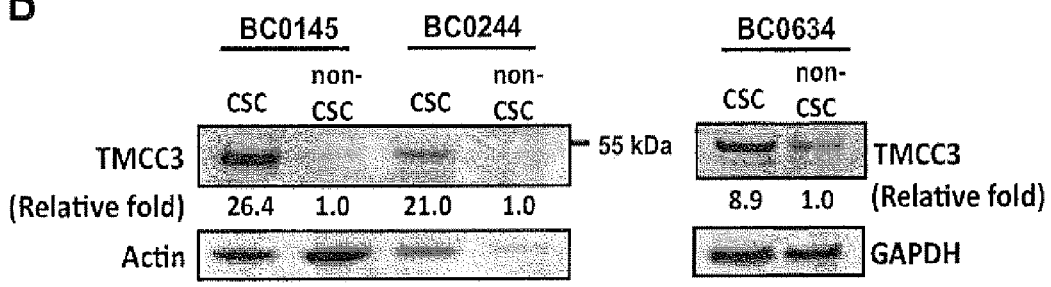
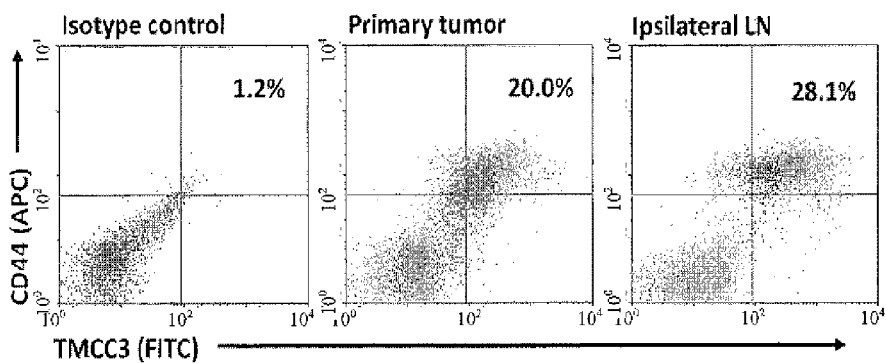
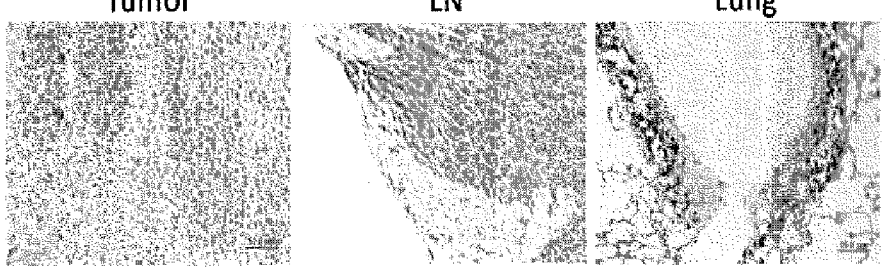

Figure 6
A
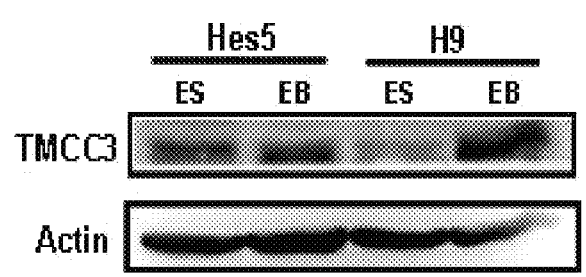
B
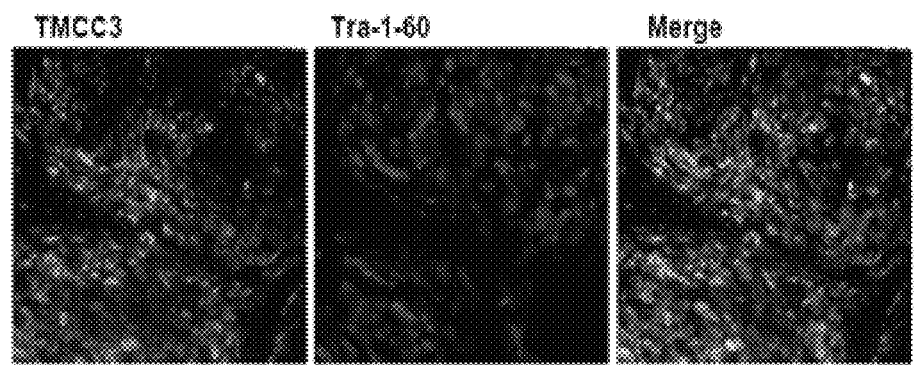

Figure 8
Map of TMCC3$_{\Delta TM}$-Fc
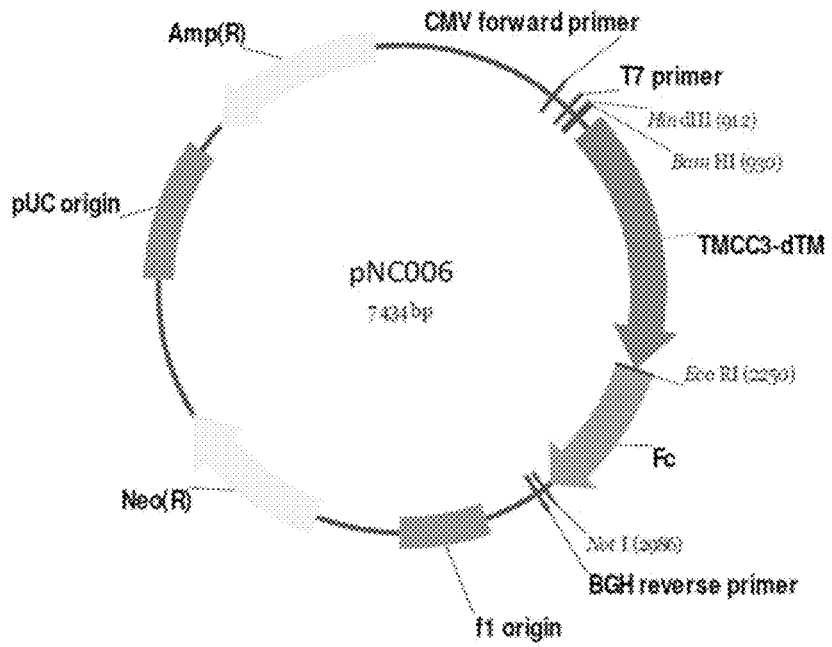
Map of TMCC3-intercoil-Fc
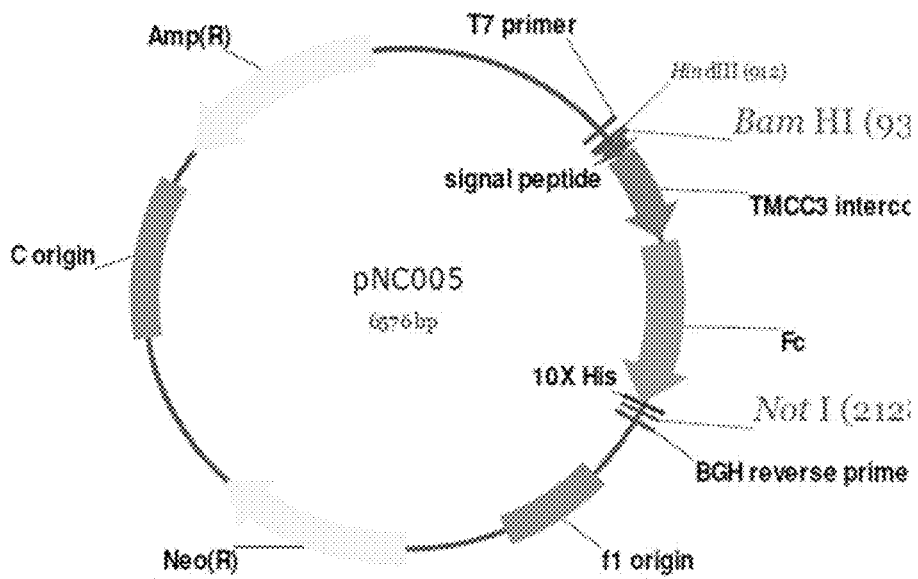

Figure 10

2nd phage ELISA result (phage titer calibrated)

| | TMCC3 Intercoil-FC | | | | | R2-FC | | | | | |
|---|---|---|---|---|---|---|---|---|---|---|---|
| | 1.5E+12 | 3.0E+11 | 6.0E+10 | 1.2E+10 | 2.4E+09 | 1.5E+12 | 3.0E+11 | 6.0E+10 | 1.2E+10 | 2.4E+09 | PFU/ml |
| 3B-5 | 2.875 | 2.957 | 2.289 | 0.822 | 0.273 | 0.017 | 0.016 | 0.006 | 0.027 | 0 | |
| 3B-8 | 2.889 | 3.12 | 2.75 | 1.617 | 0.495 | 0.008 | 0.001 | -0.006 | -0.015 | -0.027 | |
| ✗3B-12 | 3.122 | 3.137 | 2.731 | 1.264 | 0.352 | 2.412 | 1.773 | 0.903 | 0.273 | 0.041 | |
| 3B-22 | 3.016 | 2.953 | 2.853 | 1.982 | 0.667 | 0.054 | 0.025 | 0.018 | 0.016 | 0.017 | |
| 3B-45 | 3.026 | 2.942 | 2.347 | 0.942 | 0.287 | 0.013 | 0.01 | 0.004 | 0.002 | 0.002 | |
| 3B-65 | 2.519 | 1.51 | 0.425 | 0.139 | 0.064 | 0.145 | 0.037 | 0.023 | 0.02 | 0.02 | |
| 3B-66 | 3.046 | 3.049 | 2.594 | 1.59 | 0.467 | 0.015 | 0.015 | 0.01 | 0.01 | 0.005 | |
| 4-62 | 2.996 | 3.096 | 2.787 | 1.691 | 0.565 | 0.017 | 0.002 | -0.008 | -0.012 | -0.009 | |
| ✗4-65 | 2.96 | 3.098 | 2.779 | 1.853 | 0.63 | 1 | 0.129 | 0.038 | 0.026 | 0.026 | |
| 4-84 | 3.096 | 3.091 | 2.91 | 2.286 | 0.898 | 0.036 | 0.016 | 0.007 | 0.008 | 0.003 | |
| ✗4-87 | 2.964 | 3.11 | 2.826 | 2.252 | 0.92 | 2.82 | 2.265 | 0.996 | 0.311 | 0.084 | |
| ✗3B-94D | 2.71 | 2.595 | 1.714 | 0.687 | 0.223 | 1.993 | 1.354 | 0.547 | 0.145 | 0.018 | |
| ✗4A-85 | 2.628 | 2.621 | 2.524 | 1.664 | 0.668 | 2.318 | 2.163 | 1.574 | 0.762 | 0.175 | |

TMCC3 intercoil-Fc-10His binding curve of purified full-length chimeric antibodies

| | 3B-5 | 3B-8 | 3B-22 | 3B-45 | 3B-66 | 4-62 | 4-84 |
|---|---|---|---|---|---|---|---|
| $K_D$ (M) | 1.17E-08 | 2.65E-10 | 3.42E-10 | 3.51E-10 | 2.03E-10 | 1.31E-10 | 1.13E-10 |

Single-cycle kinetics assay of the anti-TMCC3 antibodies

Figure 12B
Single-cycle kinetics assay of the anti-TMCC3 antibodies
TMCC3 intercoil-Fc-10His immob. 200RU, PH5.5
Analyte concentration: 100nM, 50nM, 25nM, 12.5nM, 6.25nM
3B-8
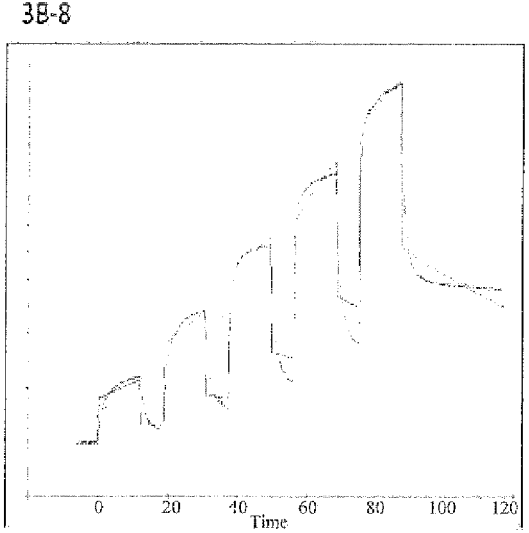
3B-45
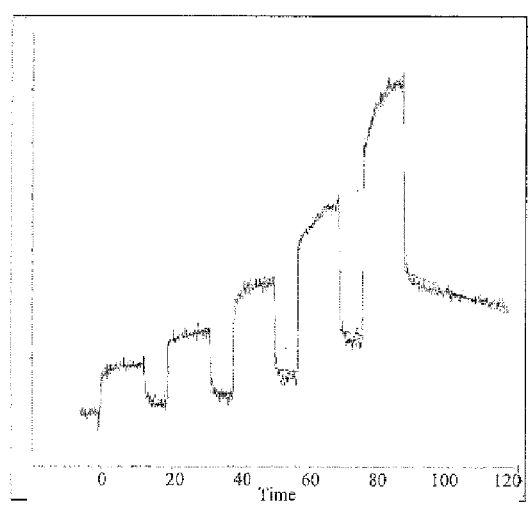

Figure 13

SPR kinetic (Biacore) analysis of the full-length anti-TMCC3 chimeric antibodies

TMCC3 intercoil-Fc-10His immob. 200RU
Analyte concentration: 100nM, 50nM, 25nM, 12.5nM, 6.25nM

| | $K_a$ (1/Ms) | $K_d$ (1/s) | $K_D$ (M) | $R_{max}$ | Chi$^2$ |
|---|---|---|---|---|---|
| 3B-5  | 9.747E+3 | 8.550E-4 | 8.772E-7 | 287.4 | 0.728 |
| 3B-8  | 1.172E+5 | 1.235E-3 | 1.053E-8 | 43.05 | 12.9 |
| 3B-22 | 5.713E+4 | 1.333E-3 | 2.334E-8 | 19.35 | 0.81 |
| 3B-45 | 3.800E+4 | 1.166E-3 | 3.068E-8 | 10.76 | 0.193 |
| 3B-66 | 1.046E+5 | 2.404E-3 | 2.299E-8 | 9.844 | 0.396 |
| 4-62  | 6.782E+5 | 1.079E-3 | 1.591E-9 | 117.4 | 18.5 |
| 4-84  | - | - | - | - | - |

Figure 14

Epitope mapping of TMCC3-specific chimeric mAbs

|  | 3B-5 | 3B-8 | 3B-22 | 3B-45 | 3B-66 | 4-62 | 4-84 |
|---|---|---|---|---|---|---|---|
| Tic1-128 recognition | + | + | +++ | + | +++ | +++ | ++ |
| Tic1-30 recognition | - | - | +++ | - | + | - | + |
| Tic25-55 recognition | - | - | - | - | - | + | - |
| Tic50-80 recognition | - | - | - | - | - | - | - |
| Tic75-105 recognition | - | - | - | - | - | - | - |
| Tic100-128 recognition | - | - | - | - | - | - | - |
| Tic1-67 recognition | - | - | +++ | ++ | +++ | + | +++ |
| Tic62-128 recognition | - | - | - | - | - | - | - |

| Tic1-30 | DISKDHLKDIHRSLKDAHVKSRTAPHCMES |
| Tic25-55 | PHCMESSKSGMPGVSLTPPVFVFNKSREFAN (SEQ ID NO: 7) |
| Tic50-80 | SREFANLIRNKFGSADNIAHLKNSLEEFRPE (SEQ ID NO: 8) |
| Tic75-105 | EEFRPEASARAYGGSATIVNKPKYGSDDECS (SEQ ID NO: 9) |
| Tic100-128 | SDDECSSGTSGSADSNGNQSFGAGGASTL (SEQ ID NO: 10) |
| Tic1-67 | DISKDHLKDIHRSLKDAHVKSRTAPHCMESSKSGMPGVSLTPPVFVFNKSREFANLIRNKFGSADNI (SEQ ID NO: 11) |
| Tic62-128 | GSADNIAHLKNSLEEFRPEASARAYGGSATIVNKPKYGSDDECSSGTSGSADSNGNQSFGAGGASTL (SEQ ID NO: 12) |

Figure 15
TMCC3-expressing Cell lines binding assay
AS-B634 (p15)
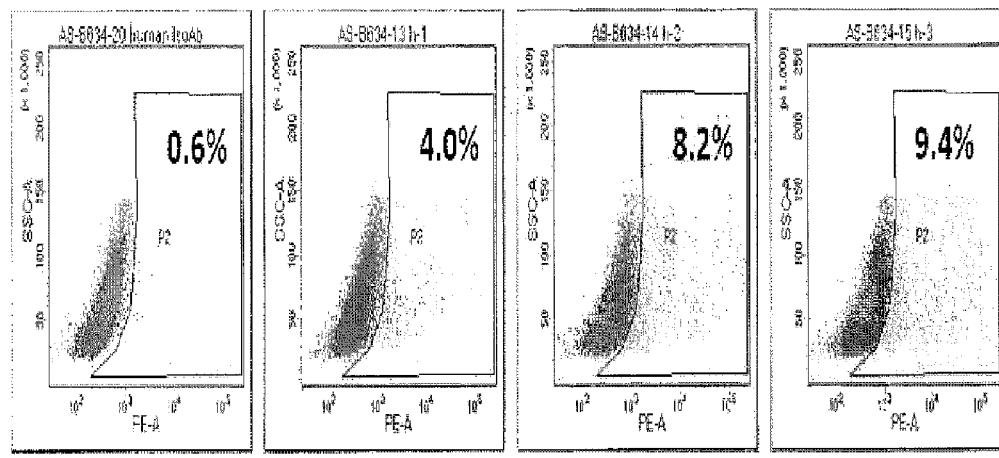
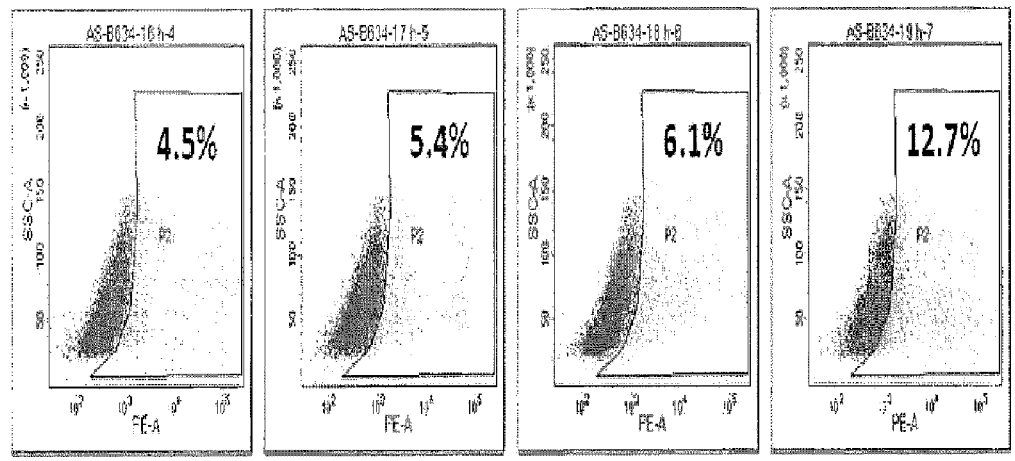

Figure 17
Recognition of anti-TMCC3 coiled linker mAb on human BCSCs (from patient No. BC0145).
Iso-type Control
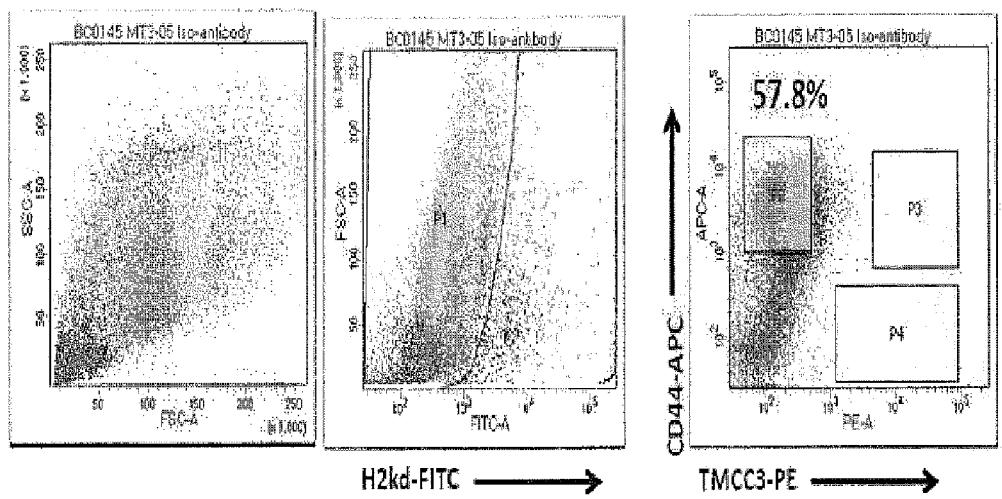
(3B-45)
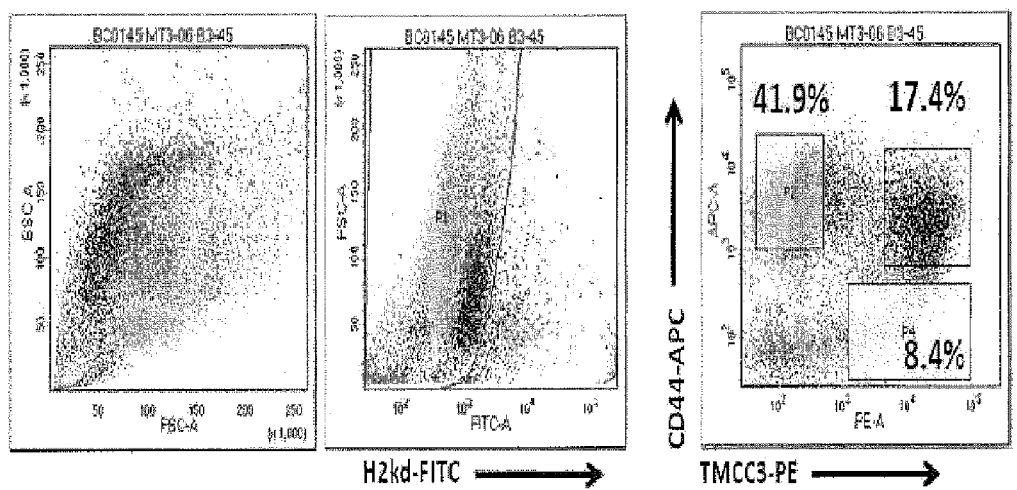

Breast cancer xenograft tumor (BC0145)

anti-H2kd-FITC
anti-CD44-APC

Human anti-TMCC3 inter-coiled-coil domain (PE)

Gating H2kd- and 7AAD negative cell population to identify the TMCC3+ cell population.

CDC activities of anti-TMCC3 on breast cancer cell-line MDA-MB231

* P = 0.03 by one-way ANOVA and Tukey's multiple comparisons test

METHODS FOR SUPPRESSING CANCER BY INHIBITION OF TMCC3

CROSS REFERENCE TO RELATED APPLICATIONS

This application claims the benefits of Provisional Application No. 61/804,751, filed on Mar. 24, 2013. The disclosure of this provisional application is incorporated by reference in its entirety.

TECHNICAL FIELD OF THE INVENTION

This invention relates to the field of cancer treatment. In particular, the application relates to biosignatures of cancer cells for early detection, prognostication and prediction of therapeutic responses for cancer. More particularly, the invention relates to methods for diagnostics and treatment of cancer via a cancer stem cell biomarker, transmembrane-coiled coil domain family 3 (TMCC3).

BACKGROUND OF THE INVENTION

The majority of cancer deaths occur as a result of recurrent or metastatic disease rather than from the effects of the primary tumor. A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop and disseminate. Many observations suggest that analogies between normal stem cells and tumorigenic cells are appropriate. Both normal stem cells and tumorigenic cells have extensive proliferative potential and the ability to give rise to new (normal or abnormal) tissues. Tumorigenic cells can be thought of as cancer stem cells (CSC) that undergo an aberrant and poorly regulated process of organogenesis analogous to what normal stem cells do. Both tumors and normal tissues are composed of heterogeneous combinations of cells, with different phenotypic characteristics and different proliferative potentials.

Cancer stem cells are believed to be a small fraction of tumor cells with stem cell-like properties, which initiate and maintain neoplastic clones. These cells have the ability to self-renew, but also give rise to progenitors that yield phenotypically diverse cancer cells but with lower tumorigenic potential. This subpopulation of stem-like cells should be highly efficient at tumor formation as compared to tumor cells that are not cancer stem cells.

Cancer stem cells (CSCs) have now been identified in a wide variety of cancers including melanomas, medulloblastomas, colon, liver, lung, prostate, breast and ovarian tumors. While CSCs do not necessarily arise from normal stem cells, they have frequently been isolated by using markers found in normal stem cells. For example, the marker CD133 has been used to identify normal adult hematopoietic and neural stem cells. CD133 has now been successfully used to enrich for CSCs from melanoma, medulloblastoma, colon and prostate tumors.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that most cancer cells lack the ability to form a new tumor such, that only the dissemination of rare cancer stem cells can lead to metastatic disease. Hence, the goal of therapy must be to identify and kill this cancer stem cell population.

Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

The existence of cancer stem cells (CSCs) have been demonstrated in a variety of human cancers. These CSCs possess the capacity for self-renewal, differentiation and display resistance to chemotherapeutic agents and radiation, which may be the cause of tumor relapse years after the clinical remission (2, 3).

Recent evidence indicates that cells within a tumor are heterogeneous and represent different stages of development (Clarke et al. 2006. Cancer Res. 66:9339-9344). In certain types of cancer, a population of cells has been identified that are termed cancer stem cells, where a cancer stem cell is defined as a cell that has the capacity to self-renew and to cause the heterogeneous lineages of cancer cells that comprise a tumor. Experimentally, such cells are ones that have the ability to generate a continuously growing tumor (Clarke et al. 2006. Cancer Res. 66:9339-9344). Cancer stem cells can arise from normal stem cells but also from cells that acquire the capacity to self-renew potentially due to a series of mutagenic events within the cell. There is considerable interest in the role of cancer stem cells in certain types of cancer. Cancer types that have been associated with the presence of cancer stem cells include breast cancer (Al-Hajj et al. 2003. PNAS 100:3983-3988), pancreatic cancer (Hermann et al. 2007. Cell Stem Cell 1:313-323), brain cancer (Singh et al. 2004. Nature 432:396-401), and testicular cancer (Houldsworth et al. 2006. J. Clin. Oncol. 24:5512-5518; Clark A. T. 2007. Stem Cell Rev. 3:49-59.

To design therapy against cancer, it is desirable to seek molecular targets of cancer or cancer stem cells that are absent from normal cells. Although many chemotherapeutic drugs and targeted therapeutic agents have improved the cure rate of cancer, recurrent disease remains to be a challenge due to the development of drug resistance. Thus, it will be important to identify biosignature for early detection, prognostication and prediction of therapeutic responses for cancer. So far, there is no reliable and validated biomarkers specific for early detection of cancer.

It is highly desirable to be able to identify these cancer stem cells using specific markers, and then use these markers to develop cancer stem cell specific therapeutics. The present invention addresses this issue.

SUMMARY OF THE INVENTION

This invention is based on the novel observation that greater expression of TMCC3 occurs in invasive breast cancer cell-lines and BCSCs, as compared to less invasive lines and non-BCSCs.

There is growing evidence showing that cancer stem cells are prone to metastasize and are relatively resistant to chemotherapy and radiation. Thus, it will be important to understand the molecular characteristics of breast cancer stem cells (BCSCs) which may lead to the development of novel targets for CSC-directed therapy.

Through phosphoproteomic analysis of BCSC and non-BCSC, we identified differential expression of the transmembrane and coiled-coil domain family 3 (TMCC3). TMCC3 belongs to TEX28 family and is predicted to be an integral membrane protein. The function of TMCC3 is unknown.

TMCC3 is essential for cell survival, proliferation, metastasis as well as self renewal and maintenance of breast cancer stem cells, and the higher expression correlates with poor clinical outcome in a variety of cancers.

We found higher expression of TMCC3 in invasive breast cancer cell line and BCSCs than less-invasive breast cancer cell lines, and non-BCSCs, respectively. In addition, TMCC3 expression was greater in distant lymph node metastasis than in primary tumor of human breast cancer xenograft in mouse. Silencing of TMCC3 led to G1 phase arrest with increased apoptotic cells, along with decreased mammosphere formation and ALDH activity, which are important features of cancer stem cell. In our previous investigation, the IGF-1R/PI3K/Akt/mTOR pathway was shown to be important for BCSCs survival and maintenance. To explore the possible involvement of TMCC3 in this pathway, we found that the Akt phosphorylation was lost in BCSCs upon TMCC3 knocked down. These findings suggest that TMCC3 is essential for breast cancer cell survival, self-renewal and metastasis. Thus, inhibition of TMCC3 may provide a new therapeutic strategy targeting stem cells.

TMCC3 could serve a biomarker for BCSCs enrichment by FACS sorting with anti-TMCC3 antibody. It also is a marker for hES cells undergoing differentiation.

Monoclonal antibodies generated against TMCC3 facilitate the phenotypic characterization of BCSCs, molecular analysis of TMCC3, and as a CSC-targeting agent. Thus, TMCC3 provides a new therapeutic strategy targeting cancer stem cells. Such endeavors provide new insight into the molecular biology of breast and other cancer and CSCs and facilitate the design of therapeutic strategies targeting cancer stem cells.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 1 shows greater expression of TMCC3 in invasive breast cancer cell-line, breast CSCs and metastatic cells. FIG. 1: TMCC3 protein expression AS-B145, H184B, T47D, MDA-MB-231, SKBR3, MCF-7 and MDA-MB-157 cell lines. FIG. 1B: protein levels of TMCC3 in BCSCs and non-BCSCs. FIG. 1C: TMCC3$^+$ cells in the tumor grown in mammary fat pad (FIG. 1C-primary tumor) and 6.9% in ipsilateral lymph node containing tumor cells (FIG. 1C-Ipsilateral LN). FIG. 1D, IHC staining for TMCC3 in lung lesion, ipsilateral lymph node with tumor, and primary tumor grown in mammary fat pad.

FIG. 2A: Kaplan-Meier analysis reveals that breast cancer patients with higher expression of TMCC3 had lower survival rate (p-value <0.05). FIG. 2B: mRNA level of TMCC3 in cancer part, as compared to normal tissue in cervical cancer, prostate cancer, pancreatic cancer, lung cancer, glioblastoma, skin cancer, hepatoma and thyroid gland papillary carcinoma. FIG. 2C: higher expression of TMCC3 correlates with poor patient outcome not only in breast cancer, but also in colorectal, Lung and ovarian cancer.

FIG. 3A: protein level of TMCC3 in mammosphere forming cells and monolayer culture (adherent cells) in MDA-MB-231 and AS-B145, respectively. FIG. 3B: sphere numbers in shRNA-TMCC3 transfected cell and control shRNA transfected cell (p-value <0.001). FIG. 3C: ALDH activity in TMCC3-silenced and control cells. FIG. 3D: numbers of mammosphere in CD44$^+$ TMCC3$^+$ H2kd$^-$ cells than CD44$^+$ TMCC3$^-$ H2kd$^-$ cell.

FIG. 4A: the relative fold of Akt$^{ser473}$ to Akt after shRNA-TMCC3 transfection as compared to non-target shRNA transfected cells. FIG. 4B: the relative fold of ERK1$^{thr202}$ to ERK1 and ERK2$^{tyr204}$ to ERK2 of non-target shRNA transfected cells at 48 and 72 hrs after shRNA-TMCC3 transfection. FIG. 4C: the relative fold of phosphor-Akt to Akt and phosphor-ERK1/2 in TMCC3-A and TMCC3-C transfected cells, respectively. FIG. 4D: the growth rate is higher in the TMCC3-A and TMCC3-C transfected cells, compared with control vector transfected cells. FIG. 4E shows that TMCC3-A and TMCC3-C transfected cells display higher cell density than control vector transfected cells.

FIG. 5A shows that the number of migrated cell decreased in TMCC3-silenced cells, compared with non-target lentiviral control cell. FIG. 5B shows the relative folds of phosphorylated FAK$^{tyr397}$ and the relative folds of phosphorylated Src$^{tyr416}$.

FIG. 6 shows expression of TMCC3 in human embryonic stem cell (hESC) and embryoid body (hEB). FIG. 6A shows higher expression of TMCC3 in 16-day outgrowth human embryoid body (hEB) than human embryonic stem cell (hESC). FIG. 6B shows TMCC3 positive cells were distributed at the outer layer of the hEB but the undifferentiated cells marked by Tra-1-60 are mainly confined to the inner part of out-growth hEB.

FIG. 8 shows two exemplary vector constructs for the production of two TMCC3 fragments. One vector is for the production of a full-length extracellular domain (i.e., TMCC3$_{ATM}$-Fc) and the other is for the production of an intercoil fragment (i.e., TMCC3-intercoil-Fc).

As shown in FIG. 9, for example, the process may involve first constructing a cDNA library from mice that have been challenged with the desired antigen (e.g., TMCC3 or a fragment thereof). The library may be constructed for the production of Fab fragments or single-chain variable fragments. The phage library containing potential Fab or scFv clones are grown in bacteria and then released with helper virus. The released phages are then allowed to bind to the antigen fragments (e.g., TMCC fragments shown in FIG. 7). Either magnetic beads or ELISA plates may be used to isolate phages that bind to the antigen fragments. The panning process may be repeated a few times to enrich the positive phage clones. Finally, after confirmation, the sequence information from the positive phage clones may be used to express the Fab or scFv.

FIG. 10 shows results of various phage clones binding to a TMCC3 intervoil-Fc fragment from a second round of panning. Also shown are bindings of these clones to a background control peptide, VEGFR2-Fc (VEGF receptor type 2 fragment). As shown in this table, several clones show significant binding to the background control peptide, which might be due to the bindings to the Fc portion that is common in both protein fragments. Therefore, these clones are not candidates for further study.

FIGS. 12A and 12B show results of binding kinetics using BIAcore. The bindings were performed using TMCC intercoil-Fc-10His to bind with clones 38-8 or 38-45. The kinetic curves show bindings using analyte concentrations of 50 nM, 25 nM, 12.5 nM, 6.25 nM, and 3.125 nM. The results in FIG. 12 A were performed with machine set for a maximum response of 900 response units at pH 5.5, while those shown in FIG. 12B were performed with machine set for a maximum response of 200 RU and pH 5.5. Based on the binding and dissociation kinetics (rates of the increases and decreases in the curves after addition of the analyte or after wash), the kinetic constants (association rates ($k_a$) and dissociation rates ($k_d$)) and the equilibrium constant (i.e., the binding constant, $K_D$) may be calculated using any suitable kinetic analysis programs.

FIG. 13 shows summary of the kinetic constants and the binding constant for various clones based on the BIAcore assays (surface plasmon resonance).

FIG. 14 shows results of epitope mapping of various antibody clones of the invention. As noted above, various TMCC3 intercoil fragments were constructed. These fragments represent deletions in the different locations in the intercoil domain. Therefore, based on different bindings to different TMCC3 intercoil fragments, the particular epitope that binds with an antibody can be deduced. For example, from this table, clone 3B-22 binds well to the full intercoil domain (Tic1-128), the fragment with the first 30 amino acids in the intercoil domain (Tic1-30) and the fragment containing the first 67 amino acids of the intercoil domain (Tic1-67). Based on these result, one can conclude that the binding epitope for the 3B-22 clone is located within the first 30 amino acids in the intercoil domain. Similarly, clone 3B-66 and 4-84 bind well to the full length (Tic1-128) and Tic1-67, but not to Tic1-30. These results indicate that their binding epitopes are located between amino acids 30 and 67.

FIG. 15 shows the abilities of various antibodies to bind to TMCC3 expressing cells (i.e., AS-B634 (p15)). As shown, mot clones bind well to the cells, particularly clones 4-84, 3B-22, and 3B-8.

FIG. 17 shows results of binding of an anti-TMCC3 coiled linker antibody (clone 3B-45) to human BSCS cells from a patient (BC0145), assayed with fluorescence cell sorting. In the top panels, the cells were treated with a negative control antibody, Iso-antibody, and the bottom panels were cells treated with anti-TMCC3 antibody (3B-45). As shown in the top panel, the cells contain about 57.8% of CD44+ cells, while the bottom panel shows that there are 41.9% that are only CD44+ and 17.4% that are both CD44+ and TMCC3+. In addition, there are about 8.4% of the cells that are CD44−, but TMCC3+.

DETAILED DESCRIPTION OF THE INVENTION

Figure 2:
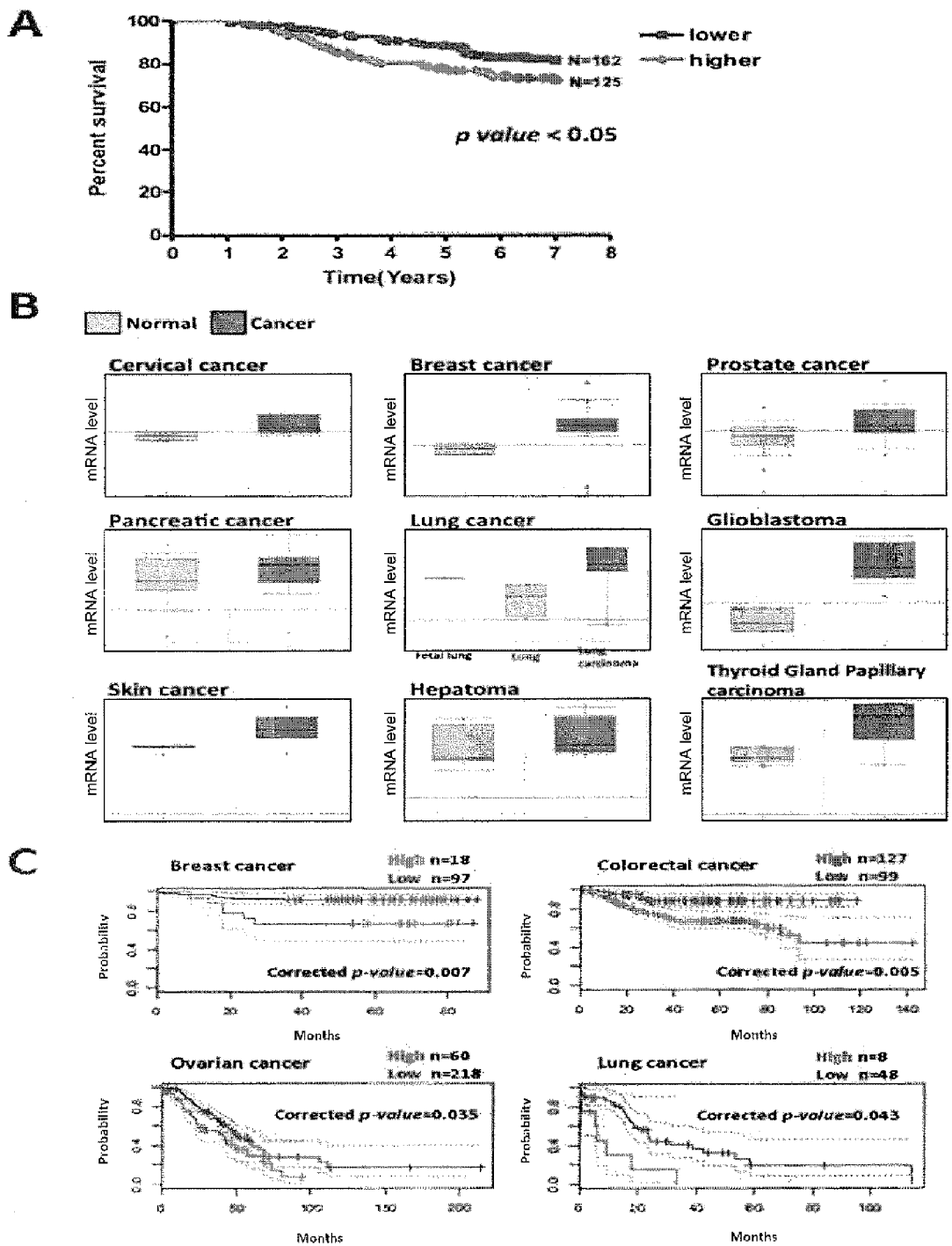
FIG. 2 shows higher expression of TMCC3 in various cancer tissue and correlation with poor clinical outcome.

Embodiments of the invention relate to methods of cancer diagnosis and treatments based on TMCC3. The transmembrane and coiled-coil domains protein 3 (TMCC3) belongs to TEX28 family and is predicted to be an integral membrane protein. The function of TMCC3 is unknown. Our phosphoproteomic analysis of breast cancer stem cells (BCSCs) and non-BCSCs revealed more phosphorylated TMCC3 in BCSCs than in non-BCSCs. The human TMCC3 gene is located in chromosome 12 and the amino acid sequence of the TMCC3 protein (SEQ ID NO: 1) is shown in Table 1.

TABLE 1

The amino acid sequence of the human TMCC3 protein (SEQ ID NO: 1)

```
                                                   (SEQ ID NO: 1)
         10         20         30         40
  MPGSDTALTV DRTYSYPGRH HRCKSRVERH DMNTLSLPLN 50         60         70         80
  IRRGGSDTNL NFDVPDGILD FHKVKLTADS LKQKILKVTE 90        100        110        120
  QIKIEQTSRD GNVAEYLKLV NNADKQQAGR IKQVFEKKNQ 130        140        150        160
  KSAHSIAQLQ KKLEQYHRKL REIEQNGASR SSKDISKDHL 170        180        190        200
  KDIHRSLKDA HVKSRTAPHC MESSKSGMPG VSLTPPVFVF 210        220        230        240
  NKSREFANLI RNKFGSADNI AHLKNSLEEF RPEASARAYG 250        260        270        280
  GSATIVNKPK YGSDDECSSG TSGSADSNGN QSFGAGGAST 290        300        310        320
  LDSQGKLAVI LEELREIKDT QAQLAEDIEA LKVQFKREYG 330        340        350        360
  FISQTLQEER YRYERLEDQL HDLTDLHQHE TANLKQELAS 370        380        390        400
  IEEKVAYQAY ERSRDIQEAL ESCQTRISKL ELHQQEQQAL 410        420        430        440
  QTDTVNAKVL LGRCINVILA FMTVILVCVS TIAKFVSPMM 450        460        470
  KSRCHILGTF FAVTLLAIFC KNWDHILCAI ERMIIPR
```

Amino acid residues in peptides are abbreviated throughout as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

Examples of useful immunogenic sequences within TMCC3 include but are not limited to: VNKPKYGSDDEC-SSGTSGSADSNGNQSFGAGGASTLDSQGKLAVI (SEQ ID NO: 2).

The nucleotide sequence of TMCC3 gene cDNA (SEQ ID NO: 3) is shown in Table 2 below:

TABLE 2

The cDNA sequence of the human TMCC3 protein (SEQ ID NO: 3)

```
gi|188497713|ref|NM_020698.2|Homo sapiens
transmembrane and coiled-coil domain family 3
(TMCC3), cDNA
                                        (SEQ ID NO. 3)
AGCTGCAGCAGCCGCGCCGCCCCCTCGCCCGCGGCTCCCAGGGTGAT

CCCGAGCACAGCCGGTGGCTCGCGGCGCGGCAGCCCCAGAAGACGGG

AAAGTTCGCGGCCGGAGCGCGGAGATGCCGGGCAGCGACACGGCGCT

CACCGTGGACCGGACCTACTCGGACCCCGGCCGGCACCACCGCTGCA

AGAGCCGGGTAGAACGTCATGACATGAATACCTTAAGCCTGCCCCTG

AACATACGCCGAGGGGGGTCAGACACCAACCTCAACTTTGATGTCCC

GGATGGCATCCTGGACTTCCACAAGGTCAAACTCACTGCAGACAGCC

TGAAGCAAAAAATTCTAAAGGTAACAGAGCAGATAAAAATTGAGCAA

ACATCGCGCGATGGGAATGTTGCGGAGTATCTGAAACTAGTGAACAA

CGCAGACAAGCAGCAGGCGGGACGTATCAAGCAAGTCTTTGAGAAGA

AGAATCAGAAATCAGCTCACTCCATCGCCCAGCTGCAGAAGAAGTTA

GAGCAGTATCATCGAAAGCTCAGAGAGATCGAGCAGAATGGAGCCTC

TAGGAGCTCAAAGGACATTTCCAAAGACCACCTGAAGGATATACATC

GCTCTTTGAAAGATGCCCACGTGAAATCTCGAACTGCCCCCCATTGC

ATGGAGAGCAGCAAATCGGGCATGCCAGGGGTCTCACTTACTCCACC

TGTGTTCGTTTTCAATAAGTCCAGAGAGTTTGCCAACCTGATCCGGA

ATAAGTTTGGCAGCGCCGACAACATTGCTCACTTGAAAAATTCCTTA

GAGGAGTTTAGGCCAGAGGCGAGTGCCAGGGCCTACGGGGGCAGCGC

TACCATCGTGAACAAACCCAAGTATGGCAGTGATGATGAATGTTCGA

GTGGCACGTCAGGCTCGGCCGACAGTAACGGAAACCAGTCGTTTGGG

GCTGGTGGAGCCAGCACACTGGACAGCCAGGGCAAGCTCGCCGTGAT

CCTGGAGGAACTGAGGGAGATCAAGGATACCCAAGCTCAGCTGGCTG

AGGACATCGAGGCACTGAAGGTGCAGTTTAAGAGAGAATATGGTTTT

ATTTCTCAGACCCTGCAAGAGGAAAGATACAGGTATGAGCGACTGGA

GGACCAGCTGCATGACCTGACGGACCTGCATCAGCATGAGACAGCCA

ACCTGAAGCAGGAGCTGGCCAGCATTGAGGAGAAGGTGGCCTACCAG

GCCTACGAGCGCTCGCGGGACATCCAGGAAGCCTTGGAATCCTGCCA

GACTCGCATTTCTAAGCTGGAGCTCCACCAGCAAGAGCAGCAAGCTC

TGCAGACAGACACCGTGAATGCTAAAGTTCTCCTGGGGAGGTGCATC

AACGTGATCCTGGCCTTCATGACTGTCATCTTAGTGTGTGTGTCCAC
```

TABLE 2-continued

The cDNA sequence of the human TMCC3 protein (SEQ ID NO: 3)

CATCGCGAAGTTCGTCTCACCCATGATGAAGAGTCGCTGCCACATTC

TTGGCACCTTCTTTGCCGTGACTCTTCTTGCTATATTTTGTAAAAAC

TGGGACCATATCCTGTGTGCCATAGAAAGGATGATAATACCAAGATG

AAGCCACTGGTTCCTGCCTTCAAGTTCTTTCAAGTTTTTATTTTAAA

GAAAACTCTGTGCATACTACCAAATTTTACAGTGAATGATTGTGCGG

ACTCGTGTGTAAGAAAAACTAGGACTGTGTGGTGTAAATAACTACAA

TTCTCTTAACTCCGTAGCAGTTGCCAACTCAGTCCTTGTACTTCGTT

AACACGAATCTGTTTCAGAGCTCTCCTACCTTGCTCACTGCCTTAAT

CAGACCGATTTCCTGCCCACCTGACCAGCCCAGCGTGGTAAACCTCT

GTATATTGAGACCTTGGCATAATTGGTGATCCTGAAGAAAGAGGTCT

CTCTCCTAAGTCTCTGTCAGAATTGAGCTTCACAATTGCTAATGGTT

GTTTTCTGTGAGTCCTATAAAAAGCAAGGATATGCATGATTCAGGGAA

TGAAGAATCACAGGCTTGGGCAGTGTTAAACACTGTGGCCTATGGTCC

CCGTGTGATCCACCCTGCTTCTCTCCAGGGGACCATAGGTCCCGTCAT

GTACTCAGTGTCCACAGCAGTCAGTCGTGTATGACCCTGTAACGTGGA

AATCTTATCACACACCTGTTATCCAACAAGTCTACCTGAGGGGTTTTG

TTACACTTTAAATGGGAAGGCATAGGGATTTATGAATGGGGCTTTCAC

CTTCTCATACCCAGGCAACCAACACCTGATTTTGTCTCAACTGGCTAGC

AAATGCCCAGCCTTCAGAGTGTGCAGGAATGTTTTCAAATCCCTCATCA

GACTGTGACTTTAACATTAATTTGGAATCCTGTGAGCACTACTCTGAAG

GTTTGTGTTTTGGCAAATCTTTTTTCTTTTTTGAGACAGGGCTCTGCTA

AATATTGCTCAGGCTGGTTGCAAACTCCTTGCTTCAAGGGATCCTCCCAC

CTCAGCCTCCCAAGCAGCCGGGACTGCAGGCACAAGCCACCATGCCTGG

CTGTTTTTTGGCAAATCTTGATTGTGATAAGCCCCCCTGGAGGATATGA

TTCACTTTATGTGATTCATCTTATTCACAGGTCTGTGAGGGACTGCAAA

GCTTACTCAGGAAATGAAAACAAATGATGGTCATGTTGCAGTTTTTTCC

TTGAAGGACAACCGAACCATAGCCTCTAAAGTTCAAGTGCACTGAGGTG

TCGGAACGCTGAAAGCATGAGGAAACGAGGACGTAGGGTGTGACTGAAT

GGTGGCTAGATTAGTGGGAGCAGTTCACCTGGATGAAGATTGAGAGCAT

CGTCTTTGAGAAGTGAAAGACTAGCAAGAATAAAATAAATTAAGTCCAG

TGTTTGAGCCAAGGTTGCCACCTGTCTCTTAACATCTCACTGAACATAA

GTCCTGAGGTATTAGGACGACCATACTGCCTCTGAGCTGAAAACATTCA

AAAGTTCACATCCCTGTTTGGGGGATACCATTCACCGCCTTCAGCCCAG

ATGATACTTTCCTTTAAATCTGTGTCTCTGTGTGTATAACAAAGAGGAA

GATGGAAACAATGTTCATGGAAACTGCTGTTGAGCCCCTTGTCCCACCA

CTCCCGCCATCTGCTGCAGGCAGGAAGGCATGTGAGTGTACGTTTTCTT

CCAGGAGACATCAGGTCCCCCTGGATTCAAATTAAGTGCAATATTTTGC

AAACAGCTCTTCTTAGGGAAATCTCCTGAAGGAAAAAAATGTGACAGAA

TGTTCCATAGTCTGAGAGAATGGAATCGTTGAGCATTTAGTACAAGTCC

AGTGTGTGTGAGCGGGACTTAGGCAGCTCAAGCTTGCTTTTTTTTTAA

GCGTACAATTGAGTGGTTTTAGTAAATTCACAAACTTGTTCAACCATCA

CCACTATCTAATTCCAGACTCACGCTTTTTTAAACAATAAATGTCATTT

CATGAAATCTTTGGTGATAAAGTATTTTGGATTCAGAGAAGAGCTCCCT

TACCAGTCCCACCCTGATCTCATGGCTGTCTCTCCTTTCATTGTCAGAC

TCCCCCTGGTCTACCGCGTTGATGTGTATACACTGATCTTTCAAGTCT

GGGAGACAGATAAGGAGGCCAGGTGCAAGGCAGGGAGGCAGAGAGAAT

GTTGTGCTTCCTTTAGCTTTTGTATTTCGATGGCCAGCATTACCCTTT

ACCTGTGGGCATCAGACTCAGCGTGGGCTGAGTGCTGAGTGTAACTTA

CACTCCTAAATCAAGCTGGGGCCTGGGTGGGCCCCTCTTGGTATCTGT

GAATCTTTCCAAGCACCACTTCGGACACACCAGGGATTGAGTGCTGCT

GTTAGTTTAGAGAAGGAGAGATGTCTAACCCTTGAGGTGAAGGGCTCT

GGGAGGGTCCAAGAAGACGTAGGCTTCATTTTCACACCAGCCCACACC

ATTCCAGTGCTCAGCCTAGCAAATGTGCTTTAATGCACACTTCTCAGA

CCTGTGATCCGTGTATCTTCTCCCCAGTGACAGAAGTAGAGAAGAGAA

TGGAAAGCAGCACACTCCGTCCCCTCTAGTCTGGAGCTGTTAACAGAA

TCTGCTAGAAACTAGCTTTATTCTAACATACCGTAGGATCTAAATCCT

CCTACCTGGATCATGAATTCCTTTGAAATAATTCATATTTTCATTGAC

TCTCACTAAATGTCAAATAACCTTGTTTTCACTTGGATAGGCTCAACC

TACCTGGCATATTTATTTTGCAGTCTTGTTGAAAGTTCATGAAACTTT

GTACTTTTAATAAGATGATACACTCGAAGGAAACTTTTAATCTCTGC

AGTTTATTCTCTCTTAAGGAATAAACACTCCCACTGTTTGTTCTCTTC

AATGTGTAAGGAGATTAAATGACATTTTAGAAATATTACAATTAAAAA

TAGTGATGTAGCTGTAACATATGCTGGAATTGGATATTTAATTTATGT

TTGTGTCAACTATAATCCTTTCCCCACCCCTTTCATTTATGGTAAACA

TCTTGGGCAAACCCAAAGATGGAAAGTGCTTGTTGGGTGGGTAAGCAC

CACCTGGTCTCTCAGCAAACACTCCTGAGTGGTTGAAGATGCTGGACA

TTGGATTCTAGCACTGGGTTTATCTGGTGACATAGTCTCCTGTGGGTCT

TGAGTTGGTTATTTCAAGCTCAAACTCTGAATATGATTAAACCAGAAC

ACCCCACCCCCAACTGCCAAAAAAAAAAAAAAAAAATGAAATCCATA

ATGAAACAGCAAAAAGTACTCCGTTGCTGGGTTTGGACAATGAACAT

GGGATTAGTCCCAAGTTTGTAGCTTGGAACGGTAGCATTTTTGCCTGC

GTGATCCTTGTCAGCTATTCACAGAAGGAAATCTTCCGAAACTCCGTC

TTTCATTTCAGCCGGTGAGGCTGTTATCCTTCTCTGTCAATTAGCATT

CATGTGGTTTTCGCTCTTTCCAGCTCTGTCACTCTTGTTTTCATTTAA

ATATTGCCCCACTCTGTGTTTATTGCCTTGCCATTTCTCTAGCATATC

AGGTTTAATTATGGGCTCAGTAATAATGAGGAACTAGCTTCCCTCAG

GCAACTAATTACTTTTGTCTTTTTTGGTCGGATTGTACCAAATTATT

TABLE 2-continued

The cDNA sequence of the human TMCC3
protein (SEQ ID NO: 3)

TTGCATTGAATGGGAATGTTTTTGCAGTGAATCCAGATATAGTTGTA

TTGGTTTGGAAAAACATTTAAATATATTTATTCATATGAACATGTGT

GATTAAACAACCTATTTTACATATTTCTGTAATTCTGAGGAGTGGGC

TGGGGGTAGGAAGAAATGGCACCACTTAAAATTCAGGGCTTATATGA

AGAGGTGTTTTAAGGTTAGCACATGCACAAAGGAACGAGTTGGTTTA

AAAAGATAAATCACTGCAAAGAATGAAATTGGCTTATTCACATCAAA

ACTAGATAAGATGCTAAAAAAAAAGATATGAAACAGAACTAACCTA

TAGTTTCCTGAAATCAGTACAGTTTAATTTATAAGAAGCTAGAAAGT

AATGCACCTTGATTGTTTAGGAATGATTTATGTGTTGCAATTTTAA

TTTATTTAAAGCATGTCTACTGTGTTTGTCCTAAGAGAAATATTTCA

ACAAAACGTGCTCTGTGTTTAAGATATGTTTAGGCAGTAGTTAGCAA

CTCTGAAAGTAGAAACTGGAAATGTTTATTGTGAGGCTTGTTGCAGA

ATTTCCATTTTGTGAGTTACTACTTAGTTTCATGTCAGCCTAAAATT

GTAAATTCCCTGTAGATCTTCACCCCATTGTGGTGTCATCAATGAAT

CCAAAGCAGGTGCCATTATTTTTTTAAATAAACACTTGATGTTAGCT

TTGGTGTTAAATAAAGAGGTAGATTTCTTAAATTTTAAAA

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art.

It should be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

When referring to a formulation component, it is intended that the term used, e.g., "agent," encompass not only the specified molecular entity but also its pharmaceutically acceptable analogs, including, but not limited to, salts, esters, amides, prodrugs, conjugates, active metabolites, and other such derivatives, analogs, and related compounds.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. As is understood by one skilled in the art, prevention or preventing need not achieve absolute (complete) block or avoidance of the conditions. Rather, prevention may achieve substantial (e.g., over 50%) reduction or avoidance of the diseases or conditions to be prevented. Unless otherwise indicated herein, either explicitly or by implication, if the term "treatment" (or "treating") is used without reference to possible prevention, it is intended that prevention be encompassed as well.

"Optional" or "optionally present"—as in an "optional substituent" or an "optionally present additive" means that the subsequently described component (e.g., substituent or additive) may or may not be present, so that the description includes instances where the component is present and instances where it is not.

By "pharmaceutically acceptable" is meant a material that is not biologically or otherwise undesirable, e.g., the material may be incorporated into a formulation of the invention without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to derivative or analog having the same type of pharmacological activity as the parent agent.

By an "effective" amount or a "therapeutically effective" amount of an active agent is meant a nontoxic but sufficient amount of the agent to provide a beneficial effect. The amount of active agent that is "effective" will vary from subject to subject, depending on the age and general condition of the individual, the particular active agent or agents, and the like. Unless otherwise indicated, the term "therapeutically effective" amount as used herein is intended to encompass an amount effective for the prevention of an adverse condition and/or the amelioration of an adverse condition, i.e., in addition to an amount effective for the treatment of an adverse condition.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "antigen" is defined as any substance capable of eliciting an immune response. As used herein, the term "immunogen" refers to an antigen or a substance capable of inducing the production of an antibody, such as a DNA vaccine. As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "immunologic adjuvant" refers to a substance used in conjunction with an immunogen which enhances or modifies the immune response to the immunogen.

As used herein, the term "anti-tumor immunotherapy active agent" refers to antibody generated by a vaccine of the of the present disclosure that inhibits, reduces and/or eliminates tumors.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987) J. Mol. Biol. 196, 901-917; Chothia et al. (1989) Nature 342, 877-883; Chothia et al. (1992) J. Mol. Biol. 227, 799-817; Al-Lazikani et al., J. Mol. Biol. 1997, 273(4)). Definitions of antigen combining sites are also described in the following: Ruiz et al. Nucleic Acids Res., 28, 219-221 (2000); and Lefranc Nucleic Acids Res. January 1; 29 (1):207-9 (2001); MacCallum et al., J. Mol. Biol., 262: 732-745 (1996); and Martin et al, Proc. Natl. Acad. Sci. USA, 86, 9268-9272 (1989); Martin, et al, Methods Enzymol., 203: 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids.

In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The pharmaceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Subject as used herein refers to humans and non-human primates (e.g., guerilla, macaque, marmoset), livestock animals (e.g., sheep, cow, horse, donkey, and pig), companion animals (e.g., dog, cat), laboratory test animals (e.g., mouse, rabbit, rat, guinea pig, hamster), captive wild animals (e.g., fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient. A patient can be an individual that is seeking treatment, monitoring, adjustment or modification of an existing therapeutic regimen, etc. A "cancer patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

In the context of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc.

"Cancer", "tumor," "transformed" and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CML), and multiple myeloma. In some embodiments, the compositions and methods of the present invention are useful for treating cancer.

A "cancer target" or "cancer marker" is a molecule that is differentially expressed or processed in cancer, e.g., on a cancer cell or in the cancer milieu. Exemplary cancer targets are cell surface proteins such as TMCC3 (also, e.g., cell adhesion molecules and receptors), intracellular receptors, hormones, and molecules such as proteases that are secreted by cells into the cancer milieu. Markers for specific cancers are known in the art, e.g., MUC1 expression on colon and colorectal cancers, bombesin receptors in lung cancer, and prostate specific membrane antigen (PSMA) on prostate cancer.

In some embodiments, the cancer target can be associated with a certain type of cancer cell, e.g., leukemia, myeloma, lymphoma, AML, non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least 3, 4, 5, 6, 7, 8, 9, 10 20, 50, 100, or 1000 fold higher than its average expression in a reference population. Thus, the target can be detected or measured to distinguish the cell type or types of interest from other cells. For example, AML cancer targets include Ly86, LILRA1, and CD180.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1:10,000. Hematopoietic CSCs can be identified as CD34+, similar to normal hematopoietic stem cells (HSCs). Other CSC associated markers include ALDH (breast), CD44 (breast), CD133 (glial cancers), and Notch (e.g., myelomas and neuroblastoma).

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

As used herein, the term "polypeptide" refers to any multimer or polymer of amino acid residues. A polypeptide may be composed of two or more polypeptide chains. A polypeptide includes a protein, a peptide, and an oligopeptide. A polypeptide can be linear or branched. A polypeptide can comprise modified amino acid residues, amino acid analogs or non-naturally occurring amino acid residues and can be interrupted by non-amino acid residues. Included within the definition are amino acid polymers that have been modified, whether naturally or by intervention, e.g., formation of a disulfide bond, glycosylation, lipidation, methylation, acetylation, phosphorylation, or by manipulation, such as conjugation with a labeling component.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

Differential Expression of TMCC3 Among Various Breast Cancer Cell-Lines

To study the role of TMCC3 in breast cancer, we determined the protein level of TMCC3 in several human breast cancer cell-lines, MCF-7, SKBR3, T47D, MDA-MB-157, MDA-MB-231 and AS-B145 cells. The protein amount was normalized to H184B, a human mammary epithelial cell line and expressed as the relative fold changes.

As shown in FIG. 1A, TMCC3 protein expression was highest in AS-B145 cell line with 3.9 fold over H184B. This was followed by T47D and MDA-MB-231 cells, with the relative fold of 1.5 and 1.8, respectively. Lower levels of TMCC3 were noted in less aggressive breast cancer cell lines, SKBR3, MCF-7 and MDA-MB-157 with the relative folds of 1.1, 1.1 and 1.0, respectively. Thus, it appears that more invasive cell lines such as MDA-MB-231 and AS-B145 harbor greater expression of TMCC3 at protein level than less invasive breast cancer cell lines.

BCSCs Express Higher Levels of TMCC3 Protein than Non-BCSCs

Next, we determined the TMCC3 protein levels in BCSCs. $CD24^-CD44^+H2k^{d-}$ (BCSCs) and $CD24^-CD44^-H2k^{d-}$ cells (non-BCSCs) were sorted from mouse xenograft tumor BC0145 and aldehyde dehydrogenase (ALDH) activity high (BCSCs) and ALDH activity low (non-BCSCs) cells from BC0244 and BC0634 tumors. As shown in FIG. 1B, the protein level of TMCC3 was higher in BCSCs than non-BCSCs by 26.4, 21.0 and 8.9 fold, for BC0145, BC0244 and BC0634 tumors, respectively. This is consistent with higher level of TMCC3 mRNA in BCSCs than non-BCSCs in our microarray analysis of BC0145 xenograft tumor. These findings suggest that TMCC3 may contribute not only to tumor invasion, but also to the maintenance of breast cancer stem cells.

Greater Expression of TMCC3 in Breast Cancer and Other Cancers Correlates with Poor Prognosis Our preliminary data showed higher expression of TMCC3 in invasive breast cancer cell-lines and BCSCs. To address the clinical relevance of our finding, we used a microarray database to assess the correlation of TMCC3 expression and breast cancer patient outcome. In this microarray database, the authors classified a series of 295 patients with primary breast carcinomas as having a gene-expression signature associated with either a poor prognosis or a good prognosis (van de Vijver, et al., "*A gene-expression signature as a predictor of survival in breast cancer.*"

N Engl J Med, 347: 1999-2009, 2002). As shown in FIG. 2A, the Kaplan-Meier analysis revealed that breast cancer patients with higher expression of TMCC3 had lower survival rate (p-value=0.045).

We further used an online DNA microarray database which provided at the ONCOMINE website to predict the oncogenic role of TMCC3 in various cancers. As shown in FIG. 2B, higher mRNA level of TMCC3 in cancer part than normal tissue was revealed in cervical cancer, prostate cancer, pancreatic cancer, lung cancer, glioblastoma, skin cancer, hepatoma and thyroid gland papillary carcinoma. We also used PrognoScan website to predict the participation of TMCC3 in cancer progression, and the predicted result shows the higher expression of TMCC3 correlate with poor patient outcome not only in breast cancer, but also in colorectal, Lung and ovarian cancer (FIG. 2C). These findings suggest that TMCC3 may play crucial roles in cancer progression.

Metastatic Cancer Cells Express Higher Levels of TMCC3 than Primary Tumor

To delineate the role of TMCC3 in metastasis of breast cancer, we further examined the expression of TMCC3 in metastatic lesions of breast cancer in mouse xenograft of human primary breast cancer. Two months after injection of BC0145 or BC0179 tumor in mammary fat pad of NSG mice, metastatic lesions were observed in ipsilateral lymph nodes. The lymph nodes and primary tumor part tissue in BC0145 bearing mice were harvested for staining with anti-CD44 and anti-TMCC3 antibodies. As shown in FIG. 1C, there are 4.5% $CD44^+$, $TMCC3^+$ cells in the tumor grown in mammary fat pad (FIG. 1C-primary tumor) and 6.9% in ipsilateral lymph node containing tumor cells (FIG. 1C-Ipsilateral LN). In mice bearing BC0179 xenograft, metastasis to the lung and lymph nodes were observed. As shown in FIG. 1D, IHC staining for TMCC3 was strongest in lung lesion, followed by ipsilateral lymph node with tumor, and then primary tumor grown in mammary fat pad. These findings suggest that TMCC3 may contribute to cell invasiveness and metastasis.

TMCC3 Contributes to Mammosphere Formation and ALDH Activity in BCSCs.

Figure 3:
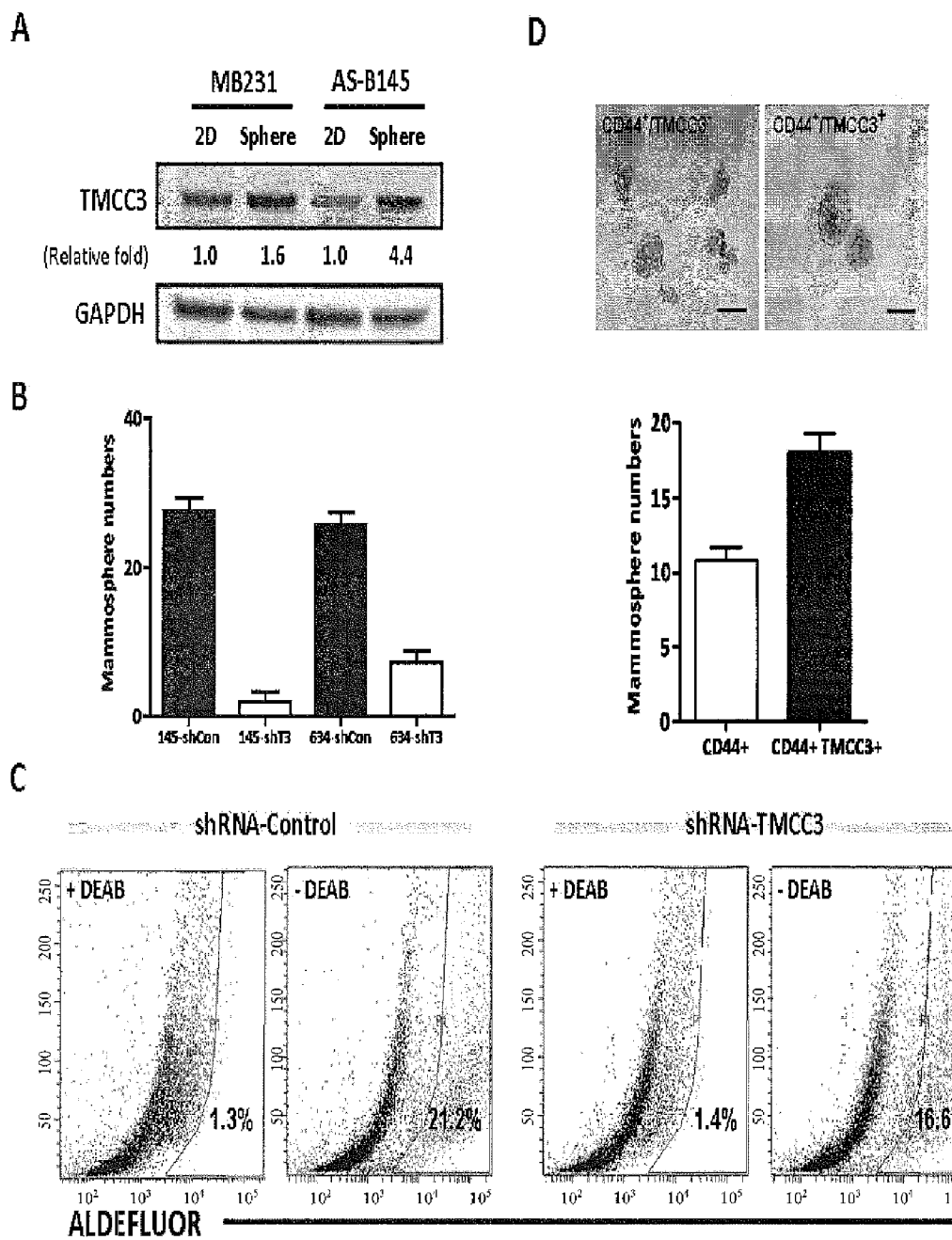
FIG. 3 shows TMCC3 contributes to mammosphere formation and ALDH population in BCSCs and could be a marker for enrichment of BCSC population.

Mammosphere formation and high ALDH activity are features of BCSCs. We found that the protein level of TMCC3 in mammosphere forming cells was higher than those in monolayer culture (adherent cells) by 1.6 and 4.4 fold in MDA-MB-231 and AS-B145, respectively (FIG. 3A). We further examined the number of sphere formation in each 1000 TMCC3-silenced (sh-T3) or control shRNA (sh-Con) transfected BCSC cell-lines, AS-B145 and AS-B634. As shown in FIG. 3B, the sphere numbers were lower in shRNA-TMCC3 transfected cell than in control shRNA transfected cell (p-value <0.001). We also determined the ALDH activity in TMCC3-silenced and control cells and found that the percent of ALDH+ cells decreased from 21.2% in control cells to 16.6% in TMCC3 knocked down cells (FIG. 3C). These observations indicate that TMCC3 plays an important role in maintaining the properties of BCSC.

Enrichment of BCSC Population by Sorting of $TMCC3^+$ Cell

To test the possibility of using TMCC3 as a marker for enrichment of BCSCs population, $CD44^+$ $TMCC3^+H2kd^-$ and $CD44^+TMCC3^-$ $H2kd^-$ cell populations from BC0145 xenograft tumor were sorted using FACS sorting with anti-TMCC3 antibody, and then examined their self-renewal capacity by mammosphere formation assay. The result shows that $CD44^+TMCC3^+H2kd^-$ cells have significantly greater capacity of mammosphere formation, than $CD44^+$ $TMCC3^-$ $H2kd^-$ cells. Not only the size, but the numbers of mammosphere are higher in $CD44^+$ $TMCC3^+H2kd^-$ cells than $CD44^+$ $TMCC3^-$ $H2kd^-$ cell (FIG. 3D). This result indicates that TMCC3 can serve as a new biomarker for BCSCs enrichment and a therapeutic target for drug design in the future.

Figure 4:
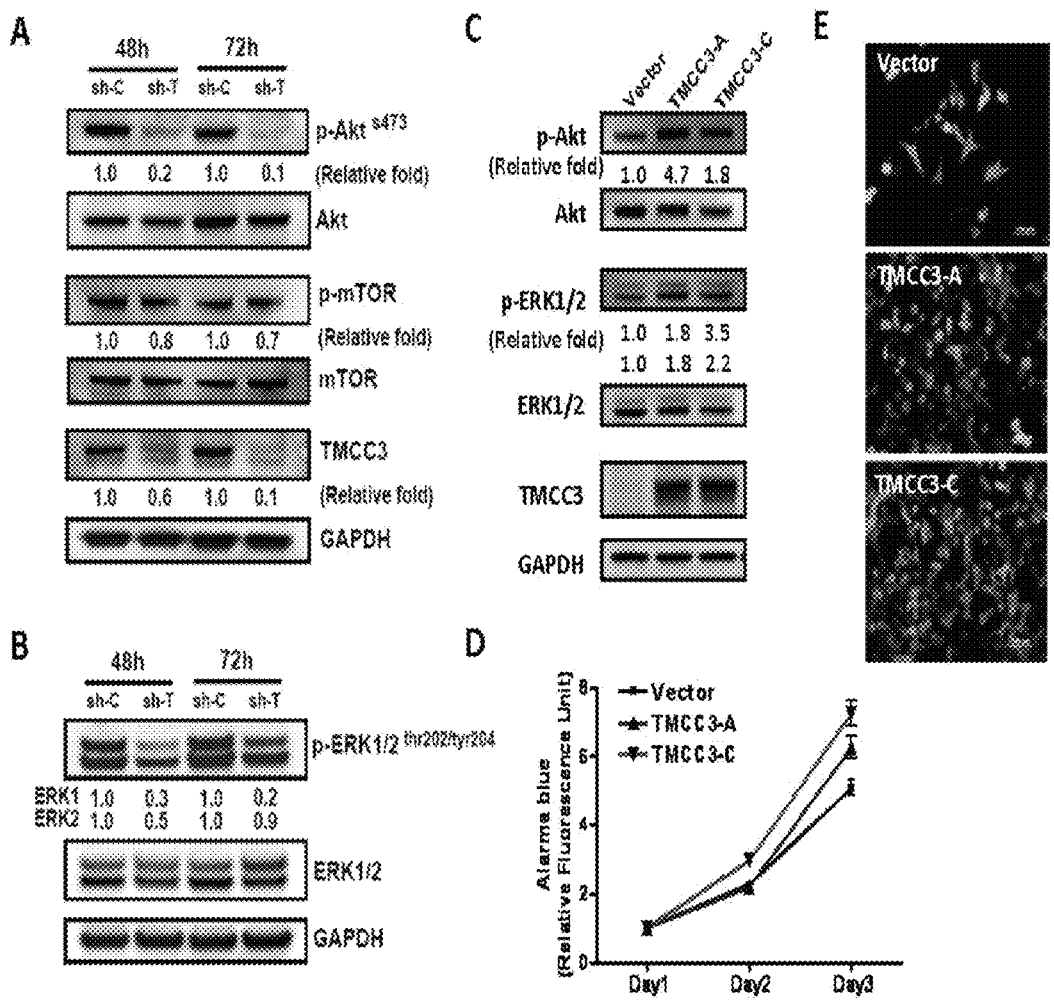
FIG. 4 shows TMCC3 is crucial for Akt and ERK1/2 signaling to regulate cell proliferation and self-renewal in BCSCs.

TMCC3 is Crucial for Akt and ERK1/2 Signaling to Regulate Cell Proliferation and Self-Renewal in BCSCs There are growing evidence showing that PI3K/Akt/mTOR and MEK/ERK signaling pathway activation are important to cancer stem cells survival and self-renewal. Recently; we have demonstrated that IGF-1R/PI3K/Akt/mTOR pathway is important for BSCSs maintenance. Previously, we discovered that phosphorylated TMCC3 (serine 216) was higher in BCSCs. To determine the possible link of TMCC3 to Akt/mTOR signaling, we examined Akt and mTOR phosphorylation in TMCC3-silenced AS-B145. As shown in FIG. 4A, the relative fold of $Akt^{ser473}$ to Akt dropped down to 0.2 and 0.1 fold at 48 and 72 hrs after shRNA-TMCC3 transfection as compared to non-target shRNA transfected cells. mTOR phosphorylation was also decreased in TMCC3 knocked down cells. The relative folds of phosphorylated mTOR were 0.8 and 0.7 at 48 and 72 hrs post transfection, respectively. These results show that TMCC3 is important for Akt activation and also contributes to mTOR activation. We further examined ERK1/2 phophorylation in TMCC3-silenced AS-B145. As shown in FIG. 4B, the relative fold of $ERK1^{thr202}$ to ERK1 dropped down to 0.3 and 0.25 and $ERK2^{tyr204}$ to ERK2 decreased to 0.5 and 0.9 fold of non-target shRNA transfected cells at 48 and 72 hrs after shRNA-TMCC3 transfection to. These results show that TMCC3 might be the up-stream regulator of Akt/mTOR and ERK1/2 pathway and play critical role in BCSC proliferation and maintenance.

Further, TMCC3 overexpressing clones of 293T cells (TMCC3-A and TMCC3-C) were established and an empty vector (CD511B-1, carried GFP) was used as a control. FIG. 4E shows that TMCC3-A and TMCC3-C transfected cells display higher cell density than control vector transfected cells. To quantify the effect of TMCC3 overexpression, we determined the cell proliferation with alamar blue which is a redox indicator that yields a colorimetric change and a fluorescent signal in a response to a metabolic activity. As shown in FIG. 4D, the growth rate is higher in the TMCC3-A and TMCC3-C transfected cells, compared with control vector transfected cells. In addition, the transfected cells were harvested for western blotting analysis at 48 h after transfection. As shown in FIG. 4C, the relative fold of phosphor-Akt to Akt increased to 4.7 and 1.8 in TMCC3-A and TMCC3-C transfected cells, respectively and phosphor-ERK1/2 increased to 1.8/1.8 and 3.5/2.2, respectively. These findings lend further support for the crucial role of TMCC3 in cell proliferation through Akt and ERK1/2 signaling activation.

TMCC3 Contributes to Cell Migration and Metastasis Through FAK/Src Pathway

Figure 5:
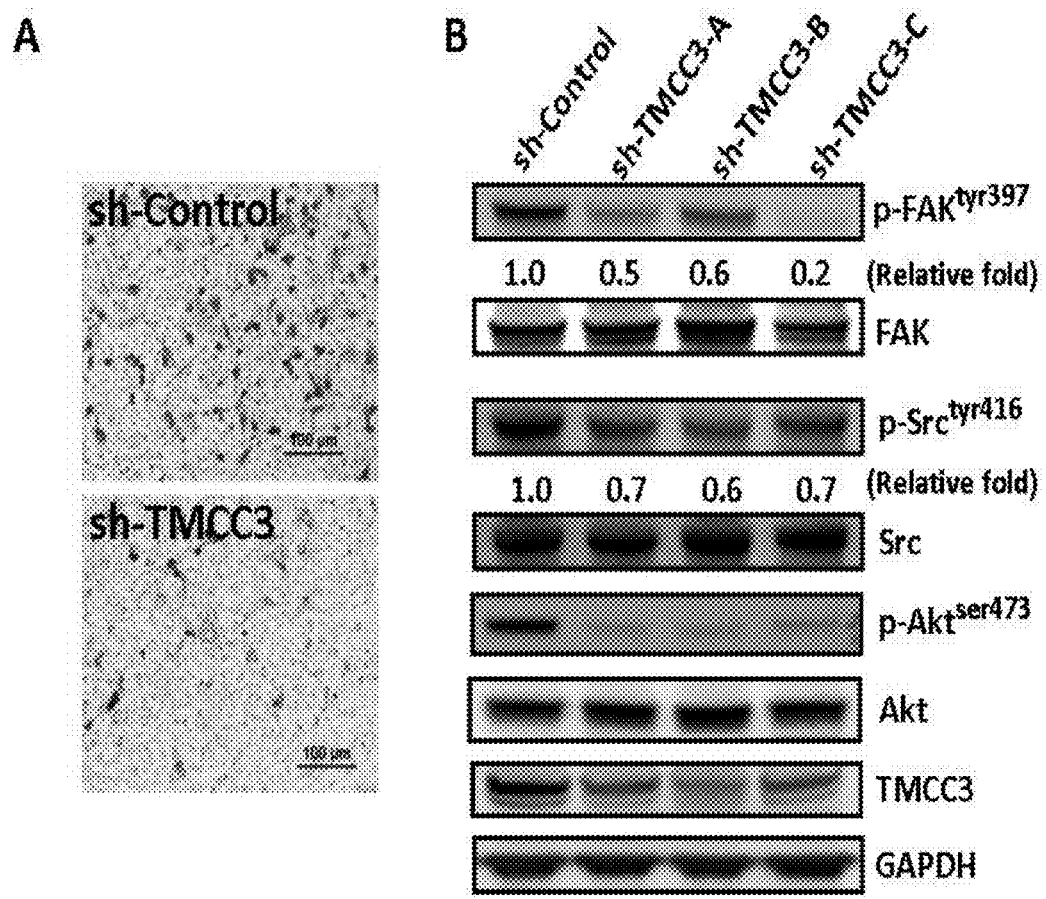
FIG. 5 shows trans-well migration assay was performed in AS-B634 cells.

In our study, we found higher TMCC3 expression in cancer cells metastatic to lymph node and lung than primary tumor grown in mammary fat pad (FIG. 1C-1D). To decipher the roles of TMCC3 in cell migration and invasion, trans-well migration assay was performed in AS-B634 cells. As shown in FIG. 5A, the number of migrated cell decreased in TMCC3-silenced cells, as compared with non-target lentiviral control cell.

It has been reported that epithelial mesenchymal transition (EMT) is important for metastasis of tumor initiating cell. However, we did not find any differences in the expression of EMT markers, including E-cadherin, N-cadherin and vimentin upon TMCC3 silencing (data not shown). FAK is a cytoplasmic tyrosine kinase identified as a key mediator of intracellular signaling triggered by integrins to regulate cell survival, migration and invasion. Previous studies have showed that integrin beta5 contributes the tumorigenicity through Src-FAK signaling pathway in breast cancer and the ablation of FAK reduced the pool of cancer stem/progenitor cells in primary tumors of FAK targeted mice, and impaired their self-renewal and migration. We thus examined whether the TMCC3 dependent cell migration correlates with the phosphorylation of FAK/Src. Indeed, we found FAK phosphorylation was decreased in TMCC3 silenced BCSCs. The relative folds of phosphorylated $FAK^{tyr397}$ were 0.5, 0.6 and 0.2 in three different shRNA-TMCC3 clones (FIG. 5B). Src phosphorylation was also decreased in TMCC3 knocked down cells. The relative folds of phosphorylated $Src^{tyr416}$ were 0.7, 0.6 and 0.7, respectively (FIG. 5B). These results indicate that TMCC3 dependent cell migration is closely associated with FAK/Src signaling pathway in BCSCs.

The sequences of the three shRNA-TMCC3 clones are as below:

TABLE 3

Sequences TMCC3 of shRNA

| Clone ID | Target sequence | Target gene |
|---|---|---|
| TRCN0000179802 | CCGGCGACAACATTGC TCACTTGAACTCGAGT TCAAGTGAGCAATGTT GTCGTTTTTG (SEQ ID NO: 4) | TMCC3 |
| TRCN0000183750 | CCGGCGTCATGACATGA ATACCTTACTCGAGTAA GGTATTCATGTCATGAC GTTTTTTG (SEQ ID NO: 5) | TMCC3 |
| TRCN0000180412 | CCGGGATGGGAATGTTGC GGAGTATCTCGAGATACT CCGCAACATTCCCATCTT TTTTG (SEQ ID NO: 6) | TMCC3 | hEB Expresses Higher Levels of TMCC3 Protein than hESCs

The expression of TMCC3 in human embryonic stem cell (hESC) and embryoid body (hEB) were also determined. We found higher expression of TMCC3 in 16-day outgrowth hEB than hESC (FIG. 6A). This phenomenon was observed in Hes5 and H9 derived embryonic body. Furthermore, TMCC3 positive cells were distributed at the outer layer of the hEB, but the undifferentiated cells marked by Tra-1-60 are mainly confined to the inner part of out-growth hEB, as shown in FIG. 6B, and there was no colocalization between TMCC3 and Tra-1-60 in hEB. This suggests that TMCC3 may mark for more differentiated cells within hEB.

TMCC3-Associated Disorders

TMCC3-associated disorders include cancers associated with elevated TMCC3 expression, as described below. The antibodies of the invention can be used for diagnosis and monitoring of these disorders, as well as targeted therapy, e.g., in the case of delivering a chemotherapeutic (or cytotoxic) agent specifically to a TMCC3-expressing cancer cell. In some cases, the targeted therapy can comprise contacting a TMCC3-expressing cell with an antibody, as described herein.

TMCC3 is associated with cancer cells and cancer stem cells, and binding TMCC3 (e.g., with a TMCC3 specific antibody, or a TMCC3 specific antibody linked to a cytotoxic agent) can effectively inhibit cancer cell growth. The present TMCC3 specific antibodies can also be used for diagnosis or localization of a TMCC3 expressing cancer, optionally followed by targeted therapy using a TMCC3 specific antibody (e.g., the same antibody, or a different TMCC3 specific antibody with different binding characteristics).

The results described herein provide the first demonstration that TMCC3 is expressed in invasive breast cancer cell-lines and BCSCs and other cancer cell lines. TMCC3 specific antibodies can thus be used to target breast cancer cells (e.g., for diagnostic and/or therapeutic applications) as well as the other cancers associated with TMCC3 expression. Higher than normal TMCC3 expression was observed in cervical cancer, prostate cancer, pancreatic cancer, lung cancer, glioblastoma, skin cancer, hepatoma and thyroid gland papillary carcinoma. Higher expression of TMCC3 also correlates with poor patient outcome not only in breast cancer, but also in colorectal, lung and ovarian cancer.

TMCC3 Antibodies

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)).

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)).

Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)).

Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659

(1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention can also be produced in various formats, including as a Fab, a Fab', a F(ab')$_2$, a scFv, or a dAB. The antibody fragments can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. In some embodiments, the anti-TMCC3 antibody comprises F(ab')$_2$ fragments that specifically bind TMCC3. An antibody of the invention can also include a human constant region, e.g., humanized or human antibodies. See, e.g., Fundamental Immunology (Paul ed., 4d ed. 1999); Bird, et al., Science 242:423 (1988); and Huston, et al., Proc. Natl. Acad. Sci. USA 85:5879 (1988).

Methods for humanizing or primatizing non-human antibodies are also known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. Platelets 15:409, 2004 (for abciximab); Pedley et al., Br. J. Cancer 70:1126, 1994 (for an anti-CEA antibody); Chapman et al., Nature Biotech. 17:780, 1999; and Humphreys, et al., Protein Eng. Des. 20:227, 2007). The antibody or antibody fragment can also be labeled, or conjugated to a therapeutic agent as described below.

Diagnostic Applications

TMCC3-specific antibodies can thus be used for in vitro and in vivo diagnostic assays to detect TMCC3-expressing cells (e.g., BCSCs, certain solid tumor cells, and hematopoietic cancer cells as indicated herein). For example, a sample (e.g., blood sample or tissue biopsy) can be obtained from a patient and contacted with a TMCC3 antibody, and the presence of a TMCC3 expressing cell in the patient sample can be determined by detecting antibody binding. Antibody binding can be detected directly (e.g., where the antibody itself is labeled) or by using a second detection agent, such as a secondary antibody. The detectable label can be associated with an antibody of the invention, either directly, or indirectly, e.g., via a chelator or linker.

In some embodiments, the anti-TMCC3 antibody is contacted with a biological sample from an individual having or suspected of having a TMCC3 associated disorder, and antibody binding to a cell in the sample is determined, wherein higher or lower than normal antibody binding indicates that the individual has a TMCC3 associated disorder. In some embodiments, the biological sample is a blood sample or blood fraction (e.g., serum, plasma, platelets, red blood cells, white blood cells). In some embodiments, the biological sample is a tissue sample (biopsy), e.g., from a suspected tumor site, or from a tissue that is known to be affected, e.g., to determine the boundaries of a known tumor. In some embodiments, the biological sample is obtained from a site of inflammation.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Biopsy techniques are discussed, for example, in Harrison's Principles of Internal Medicine, Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In some embodiments, the method comprises preparing the biological sample for detection prior to the determining step. For example, a subpopulation of cells (e.g., white blood cells) can be separated from the rest of the sample from the individual (e.g., other blood components) or cells in a tissue can be suspended for easier detection.

In some embodiments, the percentage of TMCC3-expressing cells in the sample is determined and compared to a control, e.g., a sample from an individual or group of individuals that are known to have a TMCC3 associated disorder (positive control) or from an individual or group of individuals that are known not to have a TMCC3 associated disorder (normal, non-disease, or negative control). In some embodiments, the control is a standard range of TMCC3 expression established for a given tissue. A higher or lower than normal percentage of TMCC3 expressing cells, or higher or lower expression level, indicates that the individual has a TMCC3 associated disorder.

In some embodiments, labeled TMCC3 specific antibodies as described herein can be further associated with a therapeutic compound, e.g., to form a "theranostic" composition. For example, an anti-TMCC3 antibody described herein can be linked (directly or indirectly) to both a detectable label and a therapeutic agent, e.g., a cytotoxic agent to kill TMCC3-expressing cancer cells or CSCs. In some embodiments, a labeled TMCC3 specific antibody is used for diagnosis and/or localization of a TMCC3 expressing cancer cell, and the TMCC3 expressing cancer cell is then targeted with a separate therapeutic TMCC3 specific antibody.

Therapeutic Applications

TMCC3 is aberrantly expressed in cancer cells and cancer stem cells, and the TIM3-expressing cells in such conditions can be targeted using TMCC3-specific antibodies.

Alternately, TMCC3 binding can be used to screen for pharmaceuticals or biologics that inhibit TMCC3 function or expression. Both biologic and pharmaceuticals can comprise chemotherapeutic agents for the the prognosis, detection and therapy of breast cancer or related conditions.

A chemotherapeutic (anti-cancer) agent can be any agent capable of reducing cancer growth, interfering with cancer cell replication, directly or indirectly killing cancer cells, reducing metastasis, reducing tumor blood supply, etc. Chemotherapeutic agents thus include cytotoxic agents. Cytotoxic agents include but are not limited to saporin, taxanes, vinca alkaloids, anthracycline, and platinum-based agents. Classes of chemotherapeutic agents include but are not limited to alkylating agents, antimetabolites, e.g., methotrexate, plant alkaloids, e.g., vincristine, and antibiotics, e.g., doxorubicin as well as miscellaneous drugs that do not fall in to a particular class such as hydroxyurea. Platinum-based drugs, exemplified by cisplatin and oxaliplatin, represent a major class of chemotherapeutics. These drugs bind to DNA and interfere with replication. Taxanes, exemplified by taxol, represent another major class of chemotherapeutics. These compounds act by interfering with cytoskeletal and spindle formation to inhibit cell division, and thereby prevent growth of rapidly dividing cancer cells. Other chemotherapeutic drugs include hormonal therapy.

More than one therapeutic agent can be combined, either in the same composition, or in separate compositions. The therapeutic agent(s) can also be combined with additional therapeutic agents as appropriate for the particular individual. Common therapeutic agents provided to cancer patients include medications to address pain, nausea, anemia, infection, inflammation, and other symptoms commonly experienced by cancer patients.

In some embodiments, the methods as disclosed herein are useful for the treatment or prevention of a cancer, for example where a cancer is characterized by increased TMCC3 expression. In some embodiments the cancer comprises a cancer stem cell. In some embodiments, the cancer is a pre-cancer, and/or a malignant cancer and/or a therapy resistant cancer. In some embodiments, the cancer is a breast cancer.

In one embodiment TMCC3 expression is depressed or silenced by RNA interference-inducing (RNAi) molecule including, but not limited to, a siRNA, dsRNA, stRNA, shRNA and gene silencing variants thereof.

Also provided is a kit for diagnosing, staging and/or prognosing cancer, the metastatic behavior of cancer, in vivo imaging and/or monitoring the efficacy of a therapeutic cancer treatment, comprising a binding agent which specifically binds a TMCC3 antigen and instructions for use.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Western Blot Analysis

Cells were lysed in RIPA buffer supplemented with phosphatase and protease inhibitors and boiled after mixing with protein loading buffer. Aliquots of cell lysates were subjected to SDS-PAGE, and the proteins were transferred to PVDF membranes. The membrane lots were blocked with TBST buffer containing 3% BSA for 1 hour at room temperature and then incubated with the respective primary antibodies diluted in TBST (containing 0.05% Tween20 and 3% BSA) overnight at 4° C. Subsequently, blots were washed and incubated with appropriate secondary antibodies in TBST. Anti-phospho-mTOR (Ser 2448), mTOR, phospho-Akt (Ser 473), Akt, p-FAK (Tyr 397), FAK, p-ERK1/2 (p44/42) and ERK1/2 antibodies were obtained from Cell signaling Technology. Anti-GAPDH antibody was from GeneTex Inc.

Example 2

Mammosphere Formation Assay

Single cells were plated at a density of 1,000 cells per well in ultralow attachment plates (35 mm; Corning). Cells were grown in serum-free DMEM/F12, supplemented with B27 (1:50, Invitrogen), 20 ng/mL EGF and 20 ng/mL bFGF (BD Biosciences), and 10 ng/mL insulin (Sigma). The mammospheres were cultured for 7-10 d. Then the mammospheres with diameter >100 µm were counted.

Example 3

Aldefluor Assay and Flow Cytometry

To measure the ALDH activity of lentiviral knocked down cells, the Aldefluor assay was performed according to manufacturer's (Stemcell Technologies) guidelines. sh-TMCC3 and sh-control transfected cells were suspended in Aldefluor assay buffer containing ALDH substrate, Bodipyaminoacetaldehyde (BAAA) and incubated for 30 minutes at 37° C. To distinguish between ALDH-positive and -negative cells, a fraction of cells was incubated under identical condition in the presence of the ALDH inhibitor, diethylamino benzaldehyde (DEAB). This results in a significant decrease in the fluorescence intensity in ALDH-positive cells and was used to compensate in the flow cytometric analysis.

Example 4

Trans-Well Migration Assay $1 \times 10^5$ cells were suspended in MEM media without fetal bovine serum and seeded in the upper chamber of trans-well whereas the lower chamber was loaded with MEM complete media to form a nutrient gradient to attract cell to migrate and penetrate the trans-well. After overnight culture at 37° C., the trans-wells were washed, fixed and stained with crystal violet. After drying the insert membrane and the number of the cells on the lower side of the filter were counted under microscope.

Example 5

Immunohistochemistry Assay

Tumor and mouse organs were collected and fixed with 4% formalin and embedded in paraffin. Five μm sections were cut and mounted on microscope slides. After antigen retrieval, slides were stained with anti-TMCC3 antibody or rabbit IgG antibody as control, followed by biotin-conjugated $2^{nd}$ antibody and then streptavidine-HRP. After washing with PBS, the slides were incubated with DAB chromogen solution, and counterstained with hematoxylin. Coverslip was mounted with malinol and the slides were visualized under a light microscope.

Example 6

Cell Sorting

The mouse xenograft tumors were subjected to enzymatic digestion by incubation in RPMI1640 medium containing collagenase (1,000 U/ml), hyaluronidase (300 U/ml), and DNase I (100 μg/ml) at 37° C. for 1 h. Breast cancer cells were collected after filtration through a 100-μm cell strainer (BD Biosciences) and resuspended in RPMI1640 medium supplemented with 5% FBS. Cells were prepared in RPMI1640 containing 5% FBS and antibiotics (penicillin/streptomycin) and then labeled with anti-CD44-APC, and anti-mouse H2kd conjugated biotin antibody mixtures (BD Pharmingen). TMCC3 expression was detected by staining with rabbit anti-TMCC3 antibody (HPA014272, Sigma) followed by goat anti-rabbit IgG conjugated Alexa488. $CD44^+$, $TMCC3^+$, $H2kd^-$ and $CD44^+$, $TMCC3^-$, $H2kd^-$ cell populations were gated and sorted out respectively by FACS Aria II cell sorter (Becton Dickinson).

Example 7

Lentiviral Vector Production and Transduction

TRCN0000179802 (CCGGCGACAACATTGCTCACT-TGAACTCGAGTTCAAGTGAGCAATGTT-GTCGTTTTT TG; SEQ ID NO:4) clone, TRCN0000183750 (CCGGCGTCATGACATGAATACCT-TACTCGAGTAAGGTATTCATGTCATGACGTTTTT TG; SEQ ID NO:5) clone, TRCN0000180412 (CCGGGATGGGAATGTTGCGGAGTATCTCGAGA-TACTCCGCAACATTCCCATCTTTTT TG; SEQ ID NO:6), TRCN0000072205 (non-targeting control), pMD.G plasmid and pCMVAR8.91 plasmid were obtained form National RNAi Core Facility at the Institute of Molecular Biology, (Academia Sinica, Taipei, Taiwan). For lentiviral transduction, cells were infected with lentiviral particles at multiplicities of infection from 1 to 5. After 24 hours infection, the culture media was replaced with MEM complete medium containing 2 μg/ml puromycin for another 48 hours. The lentiviral transfected cells were then collected for further experiments, and Q-PCR or Western blotting assay were performed to confirm the knockdown efficiency.

Example 8

Generation of Antibodies Against Polypeptides

Polypeptides comprising TMCC3 or antigenic fragment thereof are synthesized or isolated from bacterial or other (e.g., yeast, baculovirus) expression systems and conjugated to rabbit serum albumin (RSA) with m-maleimido benzoic acid N-hydroxysuccinimide ester (MBS) (Pierce, Rockford, Ill.). Immunization protocols with these peptides are performed according to standard methods. Initially, a pre-bleed of the rabbits is performed prior to immunization. The first immunization includes Freund's complete adjuvant and 500 μg conjugated peptide or 100 μg purified peptide. All subsequent immunizations, performed four weeks after the previous injection, include Freund's incomplete adjuvant with the same amount of protein. Bleeds are conducted seven to ten days after the immunizations.

For affinity purification of the antibodies, the corresponding TMCC3 polypeptide is conjugated to RSA with MBS, and coupled to CNBr-activated Sepharose (Pharmacia, Uppsala, Sweden). Antiserum is diluted 10-fold in 10 mM Tris-HCl, pH 7.5, and incubated overnight with the affinity matrix. After washing, bound antibodies are eluted from the resin with 100 mM glycine, pH 2.5.

Example 9

Generation of Monoclonal Antibodies Against TMCC3 or Antigenic Fragment Thereof

A non-denaturing adjuvant (Ribi, R730, Corixa, Hamilton Mont.) is rehydrated to 4 ml in phosphate buffered saline. 100 μl of this rehydrated adjuvant is then diluted with 400 μl of Hank's Balanced Salt Solution and this is then gently mixed with the cell pellet used for immunization. Approximately 500 μg conjugated peptide or 100 μg purified peptide and Freund's complete are injected into Balb/c mice via foot-pad, once a week. After 6 weeks of weekly injection, a drop of blood is drawn from the tail of each immunized animal to test the titer of antibodies against CA polypeptides using FACS analysis. When the titer reaches at least 1:2000, the mice are sacrificed in a $CO_2$ chamber followed by cervical dislocation. Lymph nodes are harvested for hybridoma preparation. Lymphocytes from mice with the highest titer are fused with the mouse myeloma line X63-Ag8.653 using 35% polyethylene glycol 4000. On day 10 following the fusion, the hybridoma supernatants are screened for the presence of CAP-specific monoclonal antibodies by fluorescence activated cell sorting (FACS). Conditioned medium from each hybridoma is incubated for 30 minutes with a combined aliquot of PC3, Colo-205, LnCap, or Panc-1 cells. After incubation, the cell samples are washed, resuspended in 0.1 ml diluent and incubated with 1 μg/ml of FITC conjugated $F(ab')_2$ fragment of goat anti-mouse IgG for 30 min at 4° C. The cells are washed, resuspended in 0.5 ml FACS diluent and analyzed using a FACScan cell analyzer (Becton Dickinson; San Jose, Calif.). Hybridoma clones are selected for further expansion, cloning, and characterization based on their binding to the surface of one or more of cell lines which express the CA polypeptide as assessed by FACS.

Generation of Monoclonal Antibodies (mAbs) Against TMCC3 Using Phase Display

In addition to using TMCC3 protein or fragments thereof as an antigen to produce antibodies against TMCC, we have also generated mAbs against TMCC3 using phase display methods.

Figure 7:
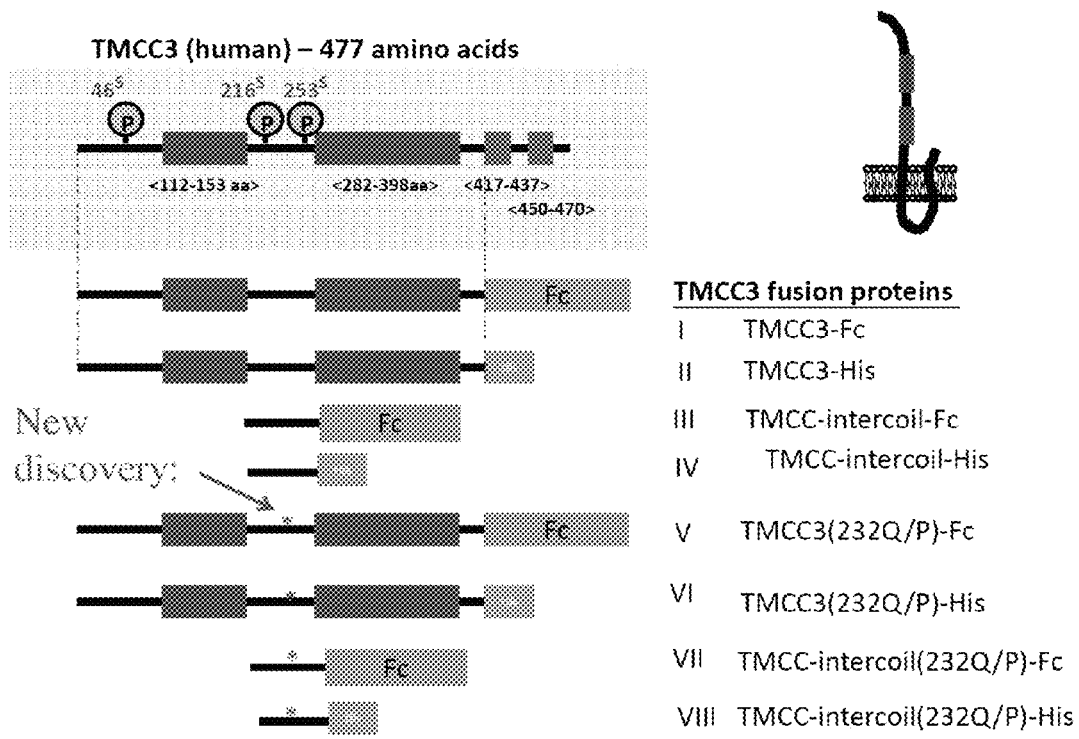
FIG. 7 shows the putative secondary structure of TMCC3, which contains an extracellular domain that comprises two coil regions struddle an intercoil region. The two transmembrane domains and a short cytoplasmic domain are located near the C-terminus of the molecule. Also shows are various fragments of TMCC extracellular domain and the intercoil domain. These fragments are constructed for phage panning and for binding assays. To facilitate the purification and detection of these fragments, these fragments are tagged in their C-terminus with an immunoglobulin constant fragment and/or a histidine tag (e.g., 10His tag). Because these fragments represent different deletions of the extracellular domain, they can also be used to map of the epitopes of the antibodies of the invention, as set forth below.

As shown in FIG. 7, the predicted secondary structures of the extracellular domain of TMCC3 includes two coiled-coiling domains linked by an intercoil domain. The first coiled coiled domain spans amino acids 112-153, and the second coiled coil domain spans amino acids 282-398. The intercoil domain (i.e., the linker) is located between amino acids 153 and 282. Antibodies that would be more useful would be binding to this extracellular domain. To facilitate phase panning, several TMCC3 fragments were constructed that include the TMCC3 extracellular domain or fragments of the extracellular domain. These protein fragments are constructed with either an Fc (antibody constant fragment) or a His tag to facilitate the purification and handling of these peptides.

These fragments may be constructed into any suitable vectors for protein expression. FIG. 8 shows two examples of two expression vectors based on the pNC vector. These produced fragments may be used to screen for phages that can bind to the TMCC3 domains as described below. Cloning a desired sequence into a commercially available vector is a routine practice for one skilled in the art. Thus, one skilled in the art would appreciated that the two vectors shown are for illustration only and are not meant to limit the scope of the invention.

Phage Display Approach

The following description provide one exemplary procedure for the phage display approach. One skilled in the art would appreciate that the various parameters and conditions provided in this example are for illustration only and these parameters may be altered or optimized without departing form the scope of the invention.

Construction of scFv/Fab Antibody Library

Figure 9:
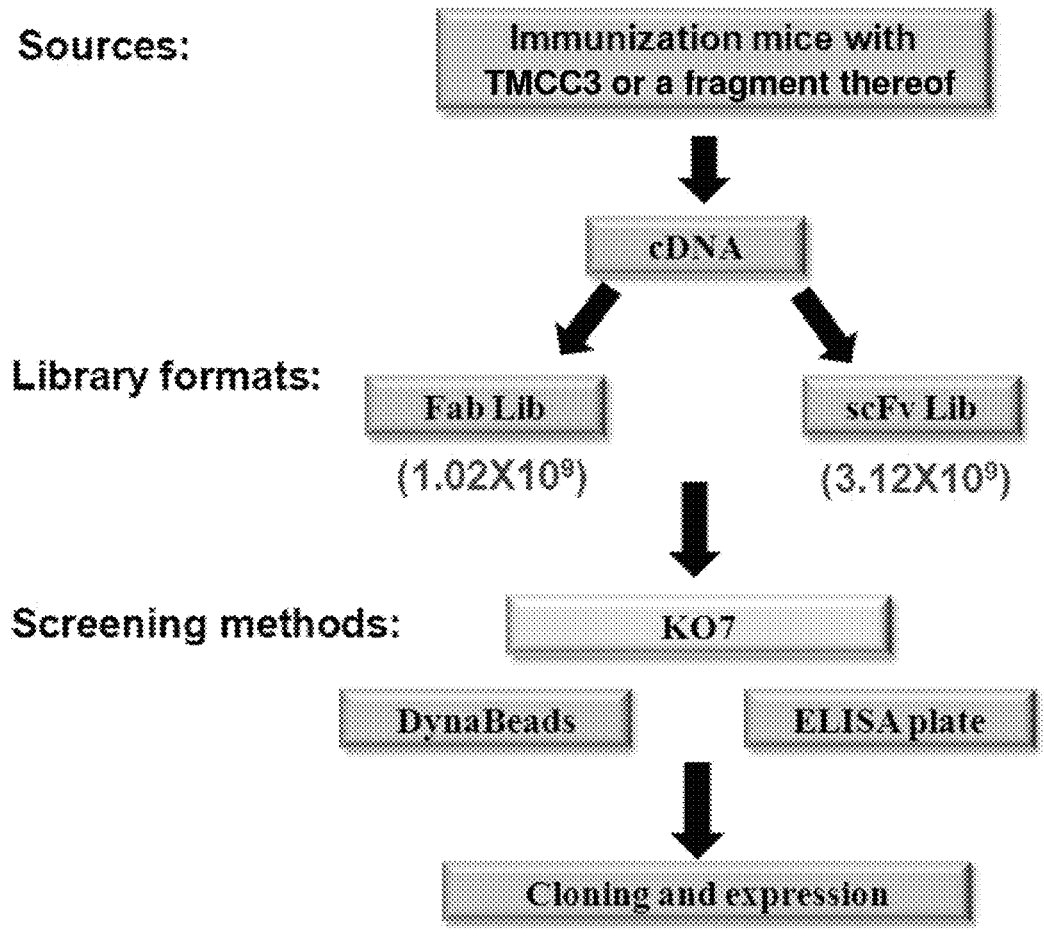
FIG. 9 shows a flow chart for using phage display to screen for antibodies (e.g., Fv variable fragments) that bind to TMCC3 or fragments thereof.

In accordance with embodiments of the invention, antibodies may be generated using phage panning. As shown in FIG. 9, a cDNA library may be constructed from immunized mice. The mice may be immunized, for example, with a recombinant TMCC3 or a fragment thereof. The mice were sacrificed and the spleens were removed to extract the total RNA. RT-PCR was then used to obtain antibody fragments (e.g., $V_H$, $V_L$, heavy chain ($F_d$) or light chain). These fragments may be used to construct a Fab library. In addition, these fragments were assembled using PCR to generate antibody cDNA fragments for scFv, which were then used to construct the scFv library. In one example, the Fab library has $6.6 \times 10^8$ diversities and the scFv library has $1.4 \times 10^9$ diversities.

Preparation of Phages for Screening

The above (scFv or Fab) library stocks each were inoculated into 2×YT medium containing 100 μg/ml ampicillin and 2% glucose (2YTAG) and grown with shaking at 37° C. until the OD (600 nm) reached 0.5. This culture was then infected with M13KO7 helper phage by adding the helper phage in a ratio of 1:20. The resultant culture was incubated in a 37° C. water bath without shaking for 30 minutes.

Then, the infected cells were collected by spinning at 4,000 rpm for 15 minutes. The cells were resuspended gently in 2×YT containing 100 μg/ml ampicillin and 25 μg/ml kanamycin (2YTAK) and incubated with shaking at 30° C. overnight.

The overnight culture was spun at 10,000 rpm for 20 min to collect the cells. PEG/NaCl (20% PEG 8000, 2.5M NaCl; 1/5 volume) was added to the supernatant. The solution was mixed and left for 1 hour or more at 4° C. It was then spun at 10,000 rpm for 20 min. The supernatant was then aspirated off.

The pellet was resuspended in 40 ml sterile water and the spun at 12,000 rpm for 10 min to remove most of the remaining bacterial debris. A 1/5 volume PEG/NaCl was added to the supernatant again. It was mixed well and left for 1 hr or more at 4° C.

It was again spun at 10,000 rpm for 20 min and the supernatant was aspirated off. The pellet was then resuspended in PBS and spun at 12,000 rpm for 10 min to remove most of the remaining bacterial debris.

The above described is one example for the preparation of phages. This example is for illustration only and not intended to limit the scope of protection. One skilled in the art would appreciate that various modifications and variations are possible. The phages may be screened using ELISA plates or Dynabeads®.

Selection Using ELISA Plates

ELISA plate (Nunc) was coated with 1 μg/100 μl antigen (e.g., the recombinant TMCC3 fragments) per well. The antigen coating was performed overnight at 4° C. in PBS, pH 7.4 or 50 mM sodium hydrogen carbonate, pH 9.6. Then, the well were rinsed 3 times with PBS and blocked with 300 μl PBS-5% skim milk (MPBS) per well for 1.5 hours at 37° C. This was followed by rinsing with PBS 3 times.

Then, 100 μl of $10''$ to $10^{12}$ phages in 5% MPBS. The solution was incubated for 90 min at 37° C., and the test solution was discarded and washed 3 times with PBS-0.05% Tween20 (PBST).

To each well was added 100 μl PBS. It was incubated for 60 min at 37° C. and washed 3 times with PBST, 1 time with PBS. The excess PBS was shaken out from the plate, and the phages were eluted by adding 100 μl 100 mM triethylamine (TEA) with rotation continuously at 37° C. for 30 min. Tris buffer (50 μl, 1M, pH 7.4) was added to the eluted 100 μl phage, for quick neutralization.

10 ml of an exponentially growing culture of *Escherichia coli* TG1 was taken and added to 150 μl of the eluted phage. Also 100 μl of the TG1 culture was added to the immunoplate. Both cultures were incubated for 30 min at 37° C. without shaking to allow for infection. Pool the 10 ml and 100 μl of the infected TG1 bacteria were polled and spun at 4000 rpm for 15 min. The pelleted bacteria was resuspended in 2×TY and plate on a large 2YTAG plate. The bacteria were allowed to grow at 30° C. overnight.

Selection Using Dynabeads®

Dynabeads® were pre-washed with 1 ml PBS three times and resuspended in 2% MPBS. Phage (0.3 ml) was mixed with 0.5 ml 2% PBSM, and the above washed Dynabeads®. The resultant suspension was pre-incubated on a rotator for 30 min.

The Dynabeads® were removed and TMCC3 fragment (biotin-labeled) was added. The resultant mixture was mixed on a rotator for 90 min. Dynabeads® were pre-washed with 1 ml PBS three times and resuspended in 2% PBSM. This was then incubated on a rotator for 90 min.

The phage-TMCC3 fragment mix was added to the equilibrated Dynabeads® on a rotator for another 30 min. The Dynabeads® were then washed with 1 ml 0.05% PBST, 2% PBSM, and PBS. The bound phages were then eluted with 1 ml 100 mM TEA. During the incubation, tubes were prepared with 0.5 ml 1M Tris, pH 7.4 to get ready for the addition of the eluted phages for quick neutralization.

6 ml of an exponentially growing culture of TG1 was taken and add the TEA eluted phage was added. Also 4 ml of the *E. coli* TG1 culture was added to the beads. Both cultures for 30 min at 37° C. (water bath) were incubated without shaking.

The infected TG1 bacterial was pooled and spun at 4000 rpm for 15 min. The pelleted bacterial in 1 ml of 2×YT was resuspended and plated on a large 2TYAG plate. The bacteria were grown at 30° C. overnight.

Preparation of Next Round Phage 5-6 ml of 2×YT containing 15% glycerol was added to the bacterial plate that had been grown overnight as described above and the colonies were loosen with a glass spreader. 50-100 of the scraped bacteria was added to 100 ml of 2×YTAG. The bacteria grew with shaking at 37° C. until the OD at 600 nm is 0.5. 10 ml of this culture with M13KO7 helper phage was infected by adding helper phage in the ratio of 1:20. The infected culture was incubated without shaking in a 37° C.

The infected cells at 4000 rpm for 15 min were spun to collect the bacteria. The pellet was resuspended gently in 50 ml of 2×YTAK and the culture was incubated with shaking at 30° C. overnight.

40 ml of the overnight culture was taken and spun at 10,000 rpm for 20 min to collect the supernatant. 1/5 volume (8 ml) PEG/NaCl was added to the supernatant, mixed well and left it for 1 hr or more at 4° C. The supernatant was spun at 10,000 rpm for 20 min and then aspirated off. The pellet was resuspended in 2 ml PBS and spun at 12000 rpm for 10 min to remove most of the remaining bacterial debris.

Screening for TMCC3-Positive Phage by ELISA

Individual colonies was incubated from the plate into 200 μl 2×YTAG 96-well plates and grew with shaking overnight at 37° C. A 96-well was used as a transfer device to transfer 50 inoculum from the plate to a second 96-well plate containing 200 μl of 2×YTAG per well and grew with shaking at 37° C. for 2 hr. 50 μl 2×YTAG with $10^9$ pfu M13KO7 helper phage was added to each well of the second plate, stand for 30 min at 37° C., and then shaken for 1 hr at 37° C.

The plate was spun at 4000 rpm for 30 min, and the supernatant was then aspirated off. The pellet was resuspended in 300 μl 2×YTAK and grew with shaking overnight at 30° C. The mixture was spun at 4000 rpm for 30 min and 100 μl of the culture supernatant was used in phage ELISA.

ELISA plates were coated with 1 μg/100 μl per well of protein antigen. Wells were rinsed for 3 times with PBS and blocked with 300 μl 2% MPBS per well for 2 hr at 37° C. Wells were rinsed for 3 times with PBS. 100 μl phage culture supernatant was added as detailed above and incubated for 90 min at 37° C. The test solution was discarded and washed three times with PBST. An appropriate dilution of HRP-anti-M13 antibody in 2% MPBS was added, incubated for 90 min at 37° C., and washed three times with PBST.

The reaction mixture was developed with substrate solution (TMB). The reaction was stopped by adding 50 μl 1 M sulfuric acid. The color should turn yellow. The OD at 650 nm and at 450 nm was read. Reading was subtracted OD 650 from OD 450.

FIG. 10 shows an exemplary result of the bio-panning using the ELISA plate methods. In this experiment, a VEGFR2-Fc fragment is used as a background control. Clones that also bind to the background control (such as 3B-12 clone) likely bind to the Fc portion of the recombinant proteins. These clones can be disregarded. As shown in FIG. 10, several clones specific to TMCC3 intercoil region were identified.

For use as therapeutic agents, antibodies should preferably have good affinities to the target molecule. The affinities and kinetics of various antibodies binding to TMCC3 may be assessed using any suitable instrument, such as ELISA or an SPR-based assay on BIAcore T100.

Figure 11:
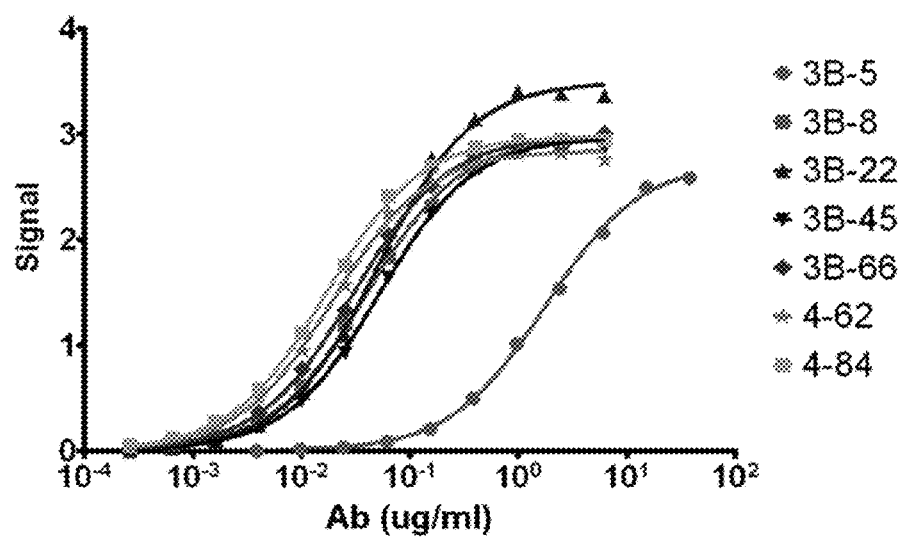
FIG. 11 shows results of ELISA binding assays of several full-length himeric antibodies that contain the variable regions from the phage screening and the constant regions of an immunoglobulin. The binding assays, which were performed using TMCC3 intercoil-Fc-10His as a binding target, revealed that most chimeric antibodies have good binding affinities (with dissociation constants in the $10^{-10}$ M range), except for 3B-5 clone. For example, clone 4-84 has a dissociation constant of $1.13 \times 10^{-10}$ M (i.e., 0.113 nM), which would be sufficient for therapeutic applications.

FIG. 11 shows the binding interactions between TMCC3 intercoiled-Fc-10His and the chimeric antibodies derived from the positive phage clones. From the binding curves, the dissociation constants of these phage clones can be calculated (shown in the Table in FIG. 11). As shown, the binding between TMCC3 intercoil-Fc-10His and most chimeric antibodies are pretty tight, with dissociation constants in the sub-nano molar (around $10^{-10}$ M) range. For example, antibody 4-84 has a dissociation constant of $1.13 \times 10^{-10}$ M.

Because antibody 4-84 is most promising as a diagnostic and therapeutic agent, it sequences have been elucidate. This antibody contains the CDR amino acid sequences as follows: CDRH1 (GFNIKDYYMH; SEQ ID NO: 13), CDRH2 (WIDPENGDTEYAPKFDG; SEQ ID NO: 14), CDRH3 (NFDY; SEQ ID NO: 15), CDRL1 (SASSSVSYMY; SEQ ID NO: 16), CDRL2 (DTSNLAS; SEQ ID NO: 17), and CDRL3 (QQYSGYPLT; SEQ ID NO: 18).

Affinity Measurements and Kinetic Analysis Using BIAcore

The binding kinetics between TMCC3 intercoiled-Fc-10His and the chimeric antibodies may be measured using BIAcore and analyzed, for example, by a single-cycle or multi-cycle kinetics (MCK) method using the associated software. The following describes one exemplary parameters and conditions for a BIAcore assay. These parameters and conditions are for references only and one skilled in the art would appreciate that variations are possible without departing from the scope of the present invention.

As an example, a TMCC3 chimeric antibody may be immobilized on CM5 chips at a density that allowed one to achieve $R_{max}$ in the range of 50-150 Response Units (RU).

In this example, the kinetic assay parameters were as follows: data collection rate 1 Hz; dual detection mode; temperature: 25° C.; concentration unit: nM; and buffer A HBS-EP. The measurements were performed with 5 replicates. The various instrument settings are as follows.

Select Capture, flow path 2-1, chip CM5, regeneration 1.

Select the Ligand Capture and set the parameters as followed, Contact time: 12 s, Flow rate: 10 μL/min, Stabilization period: 90 s. (In the range of 50-150 Response Units (RU)) (Anti-TMCC3 antibodies of BD2 and mutants as ligands).

Select the Sample and set the parameters as followed, Contact time: 300 s, Flow rate: 40 μL/min, Dissociation time: 500 s.

Select the Regeneration and set the parameters as followed, Regeneration solution: 25 mM Glycine pH1.5, Contact time: 60 s, Flow Rate: 30 μL/min, Stabilization period: 120 s.

Serial dilutions of TMCC3 fragments with the running buffer (HBS-EP+). The series concentrations obtained are 10, 5, 2.5, 1.25, 0.625, 0.3125, 0.15625, 0 and 1.25 nM (repeat). Prepare and position samples according to Rack Positions.

The results were evaluated with the BIAcoreT100 evaluation software. The binding responses were corrected for buffer effects by subtracting responses from a blank flow cell. A 1:1 Langmuir fitting model was used to estimate the $k_a$ or $k_{on}$ (association rate or on-rate) and $k_d$ or $k_{off}$ (dissociation rate or off-rate). The $K_D$ (or $K_d$) values may be determined from the ratios of $k_{off}$ and $k_{on}$ (i.e., $K_d = k_{off}/k_{on}$).

Figure 12A:
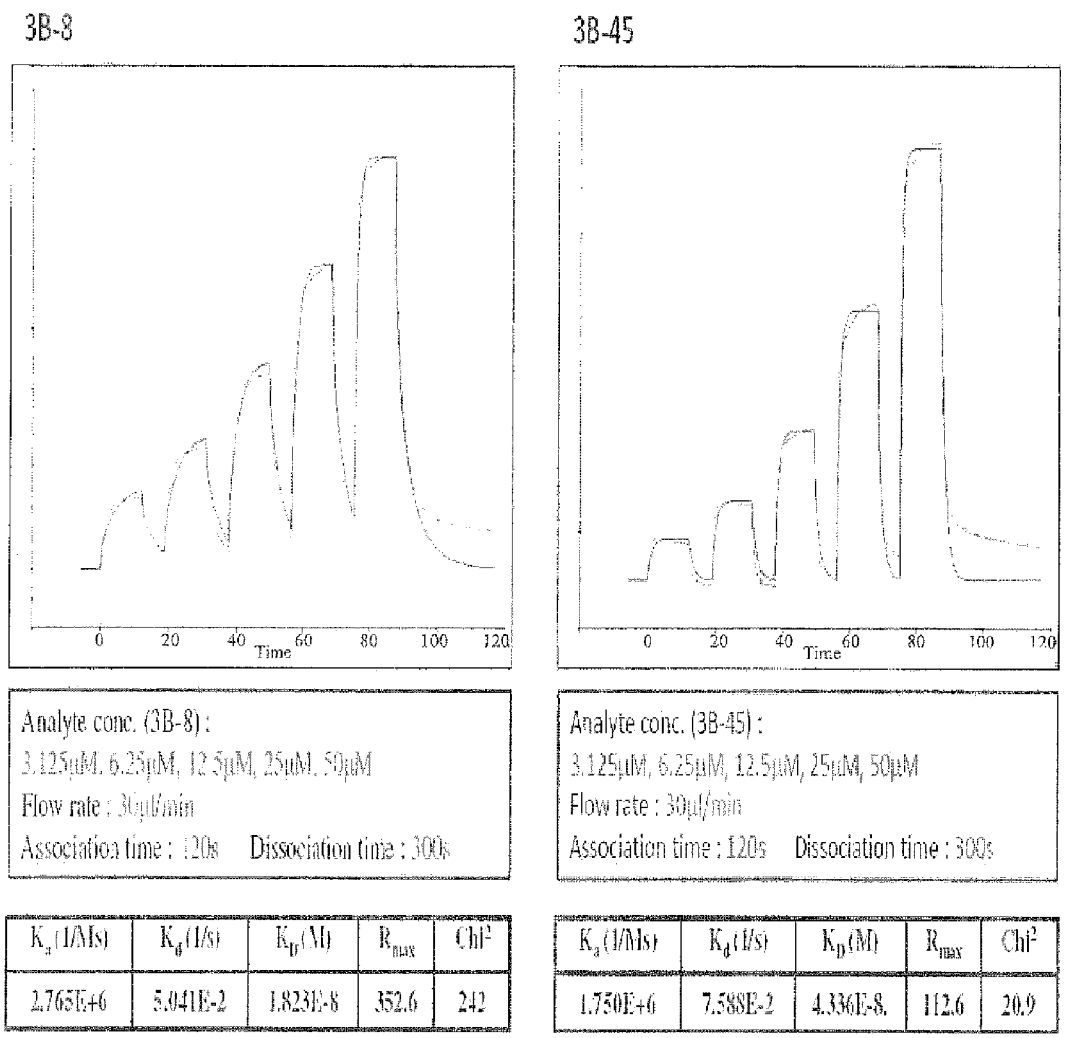

FIG. 12A shows single cycle kinetics assays of two examples using 3B-8 and 3B-45 clones to bind TMCC3 intercoil-Fc-10His (assay conditions: 900 RU, pH 5.5), and FIG. 12B shows the same assays under slightly different conditions (200 RU, pH 5.5). The corresponding kinetic parameters are shown in Tables under the graphs. Other antibodies also have similar activities. Results for these clones from the SPR kinetic (BIAcore) analysis are shown in the Table in FIG. 13.

Epitope Mapping of TMCC3-Specific Chimeric mAbs

We have also investigated the epitopes that interact with the TMCC3 specific chimeric mABs, using the various TMCC3 fragments. As shown in FIG. 13, two chimeric antibodies, 3B-22 and 4-84 show good bindings to the intercoil fragments of TMCC3. Clone 3B-22 binds fragments containing intercoil regions 1-30 peptide, suggesting that this mAb binds to an epitope located within the stretch of amino acids 1-30 in the intercoil region. On the other hand, clones 3B-66 and 4-84 bind well to longer fragments (intercoil 1-67 and 1-128 fragments), but only weakly to the shorter fragment (e.g., intercoil 1-30 fragment), suggesting that their epitopes are likely located at amino acids 30-67 of the intercoil.

Bindings of the mAbs to Cancer Cells

Some embodiments of the invention relate to methods for treating cancers using antibodies against TMCC3. The abilities of these antibodies to bind the cancer cells are investigated. The binding of the antibodies to the cancer cells are assessed using immunohistochemistry standing, followed by flow cytometry image assays. Results of binding of various antibodies to different cancer cell lines are shown in FIGS. 15-18.

Figure 16:
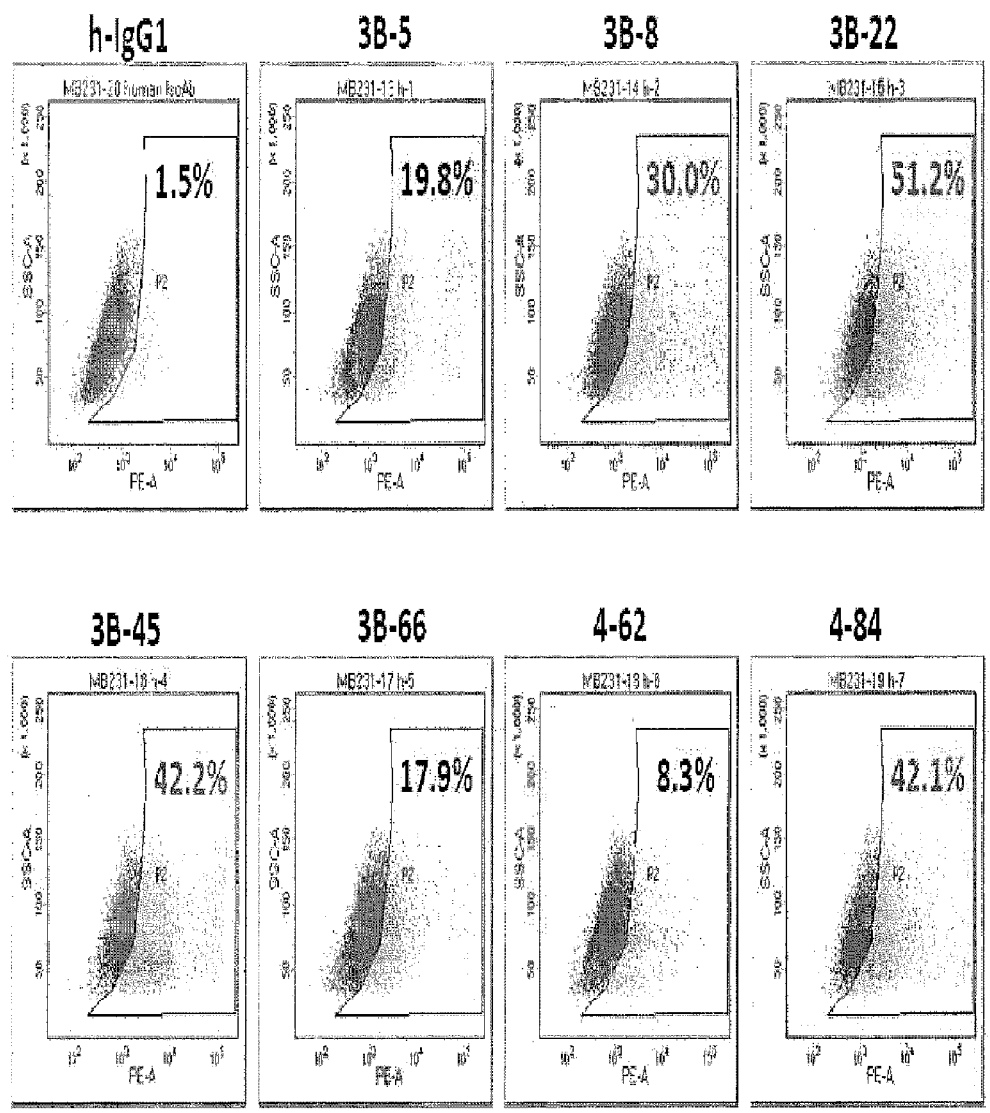
FIG. 16 shows the abilities of various antibodies to bind to another TMCC expressing cell (MDA MB231). Again, most clones bind very well to this cell line. Particularly, clones 4-84, 3B-22, 3B-45, 3B-8, 3B-5, and 3B-66 bind very well to this cell line.
Figure 18:
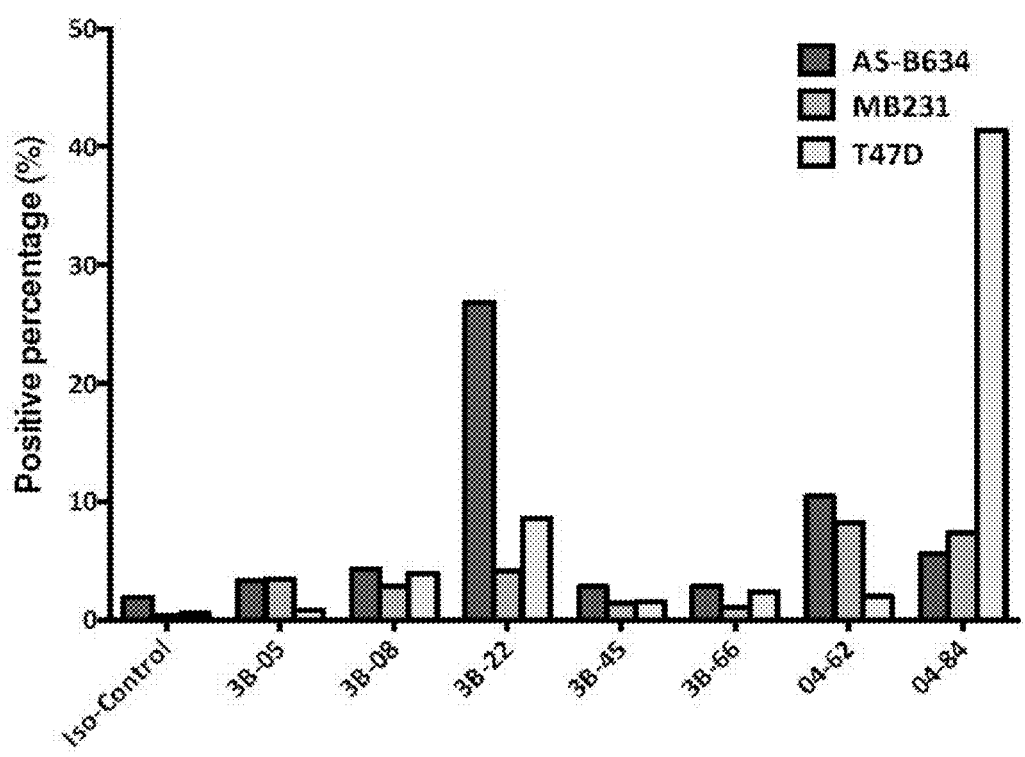
FIG. 18 shows a bar graph summarizing bindings of various antibodies to three different breast cancer cell lines (AS-B634, MDA MB231, and T47D). As shown in this bar graph, the binding of 3B-2 to AS-B634 is particularly strong, so is the binding of 4-84 to T47D.

FIG. 15 shows the results of binding to AS-B634 (p15) cells by various antibodies. FIG. 16 shows the results of binding to MDA-MB231 cells, which are triple negative, highly invasive and metastatic cells. FIG. 17 shows results for binding to human BCSC s, which was obtained from a patient. Results of various antibodies binding to different breast cancer cells (AS-B634, MDA-MB231, and T47D) are summarized as bar graphs in FIG. 18.

Figure 19:
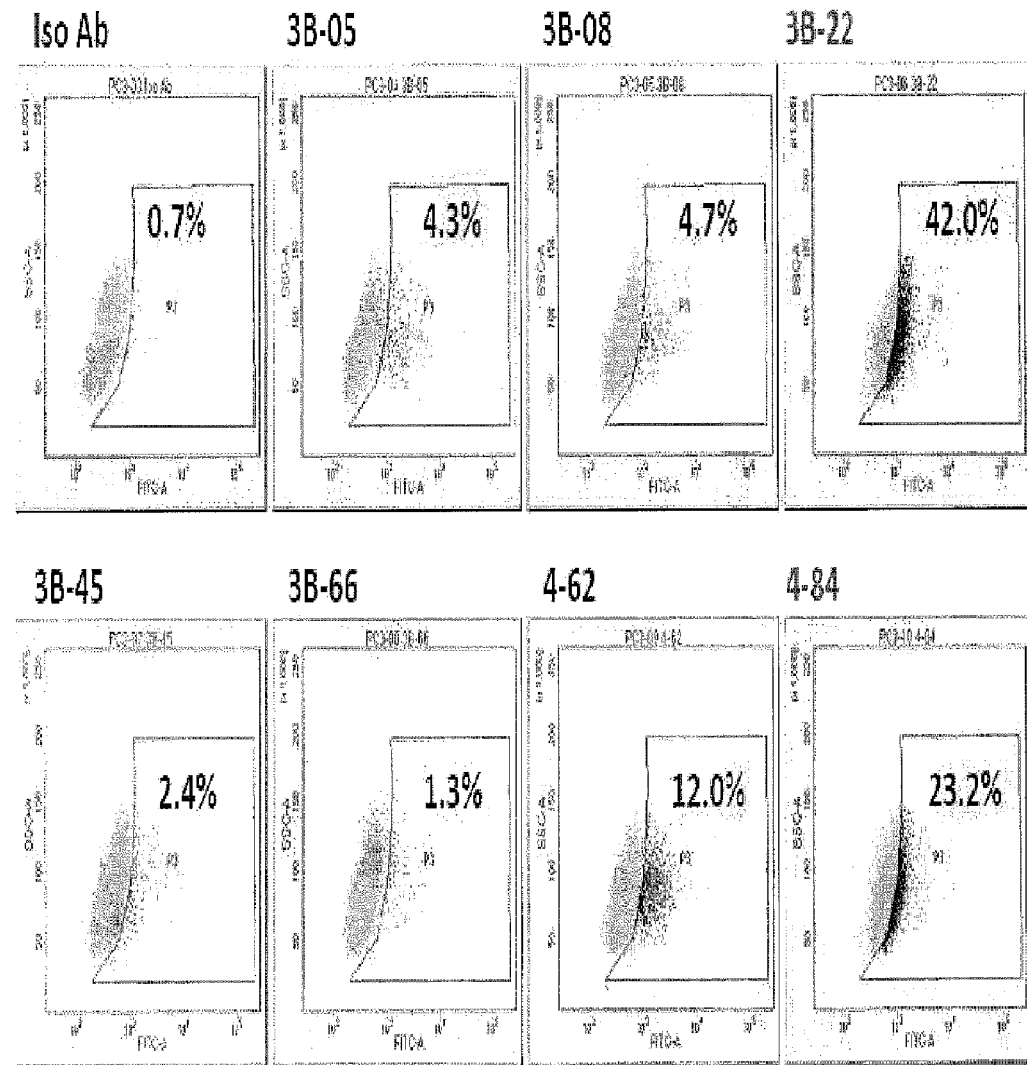
FIG. 19 shows the bindings of various antibodies to a prostate cancer cell line (PC3). As shown in these FACS data, the bindings of 3B-22 and 4-84 are very strong, while most antibodies do bind to this prostate cancer cell line.
Figure 20:
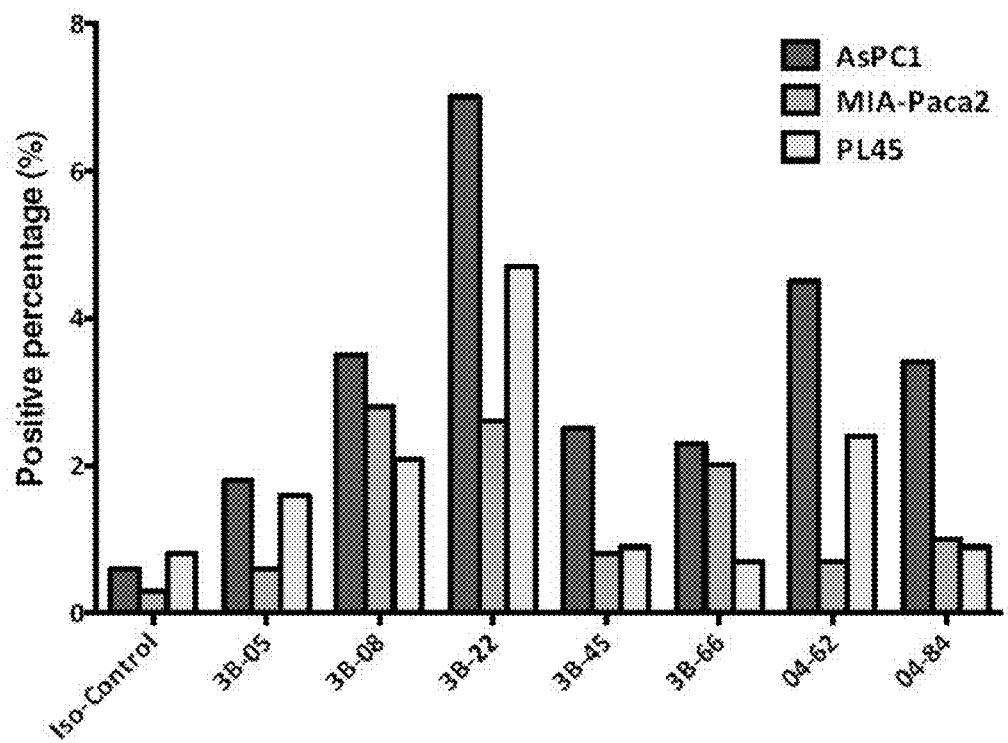
FIG. 20 shows the bindings of various antibodies to pancreatic cancer cell lines (AsPC1, MIA-Paca2, and PL45). As shown, most antibodies have significant bindings to these pancreatic cancer call lines, while the bindings of 3B-22 are particularly strong.
Figure 21:
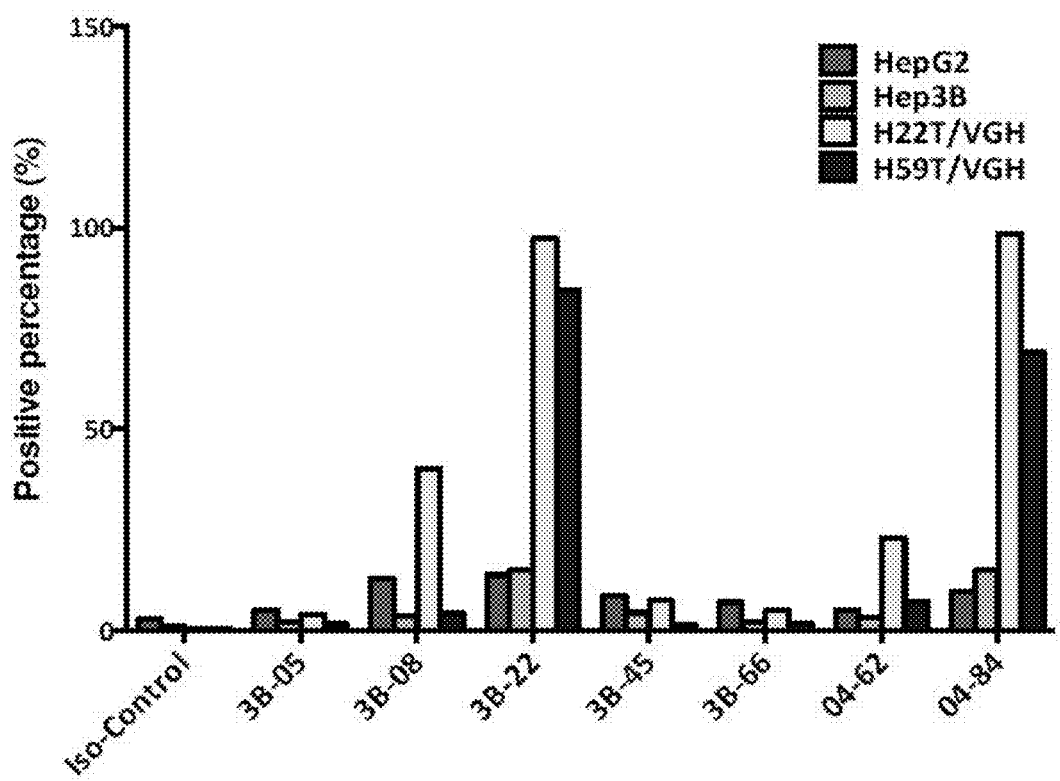
FIG. 21 shows the bindings of various antibodies to hepatoma cell lines (HepG2, Hep3B, H22T/VGH, and H59T/VGH). As shown, the bindings of 3B-22 and 4-84 are very strong, while most antibodies do bind to the test hepatoma cell line.
Figure 22:
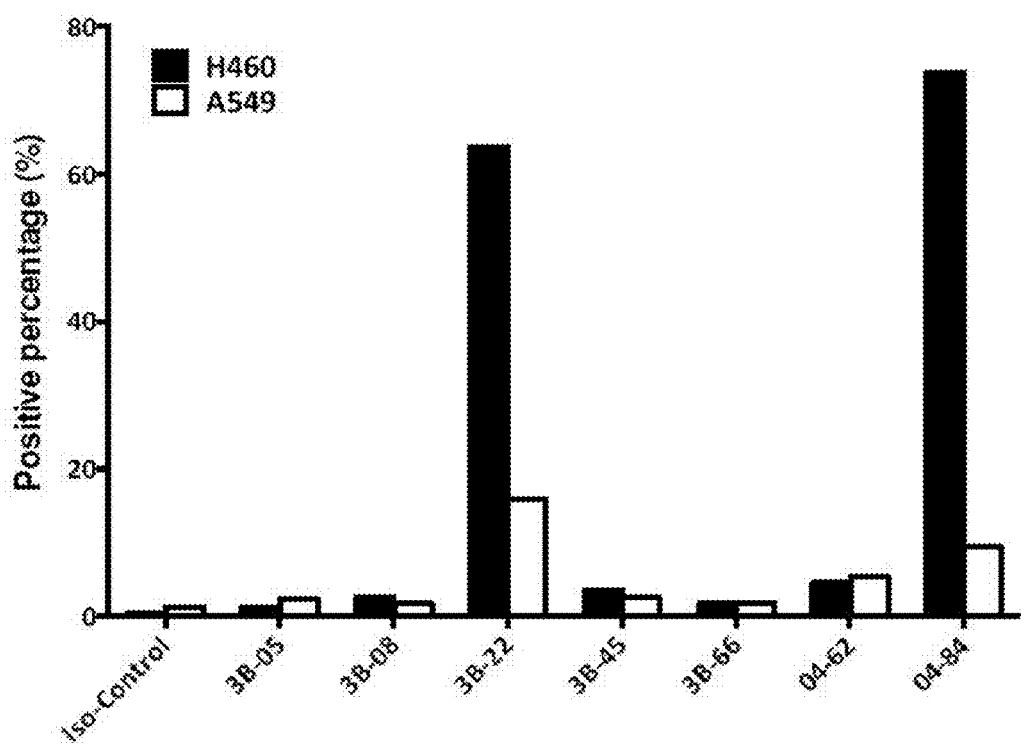
FIG. 22 shows the bindings of various antibodies to lung cancer cell lines (H460 and A549). As shown, the bindings of 3B-22 and 4-84 are very strong, while most antibodies do bind to the test hepatoma cell line.

In addition to the breast cancer cells shown in FIGS. 15-18, the antibodies also bind well to other cancer cells. FIG. 19 shows results for binding to a prostate cancer cell line (PC3). FIG. 20 shows binding results to pancreatic cancer cells (e.g., As PC1, MIA-paca1, and PL45). The abilities of various antibodies to bind the hepatoma cells (HepG2, Hep3B, H22T/VGH, and H59T/VGH) are shown in FIG. 21. As can be seen close 3B-22 and 4-84 are very strong binders to these hepatoma cells. FIG. 22 shows results of binding of various antibodies to lung cancer cells (H460 and A549). These results show that antibodies of the invention can bind tightly to various cancer cells. Therefore, these antibodies have broad applications.

Binding of Antibodies to Cancer Xenographs

Figure 23:
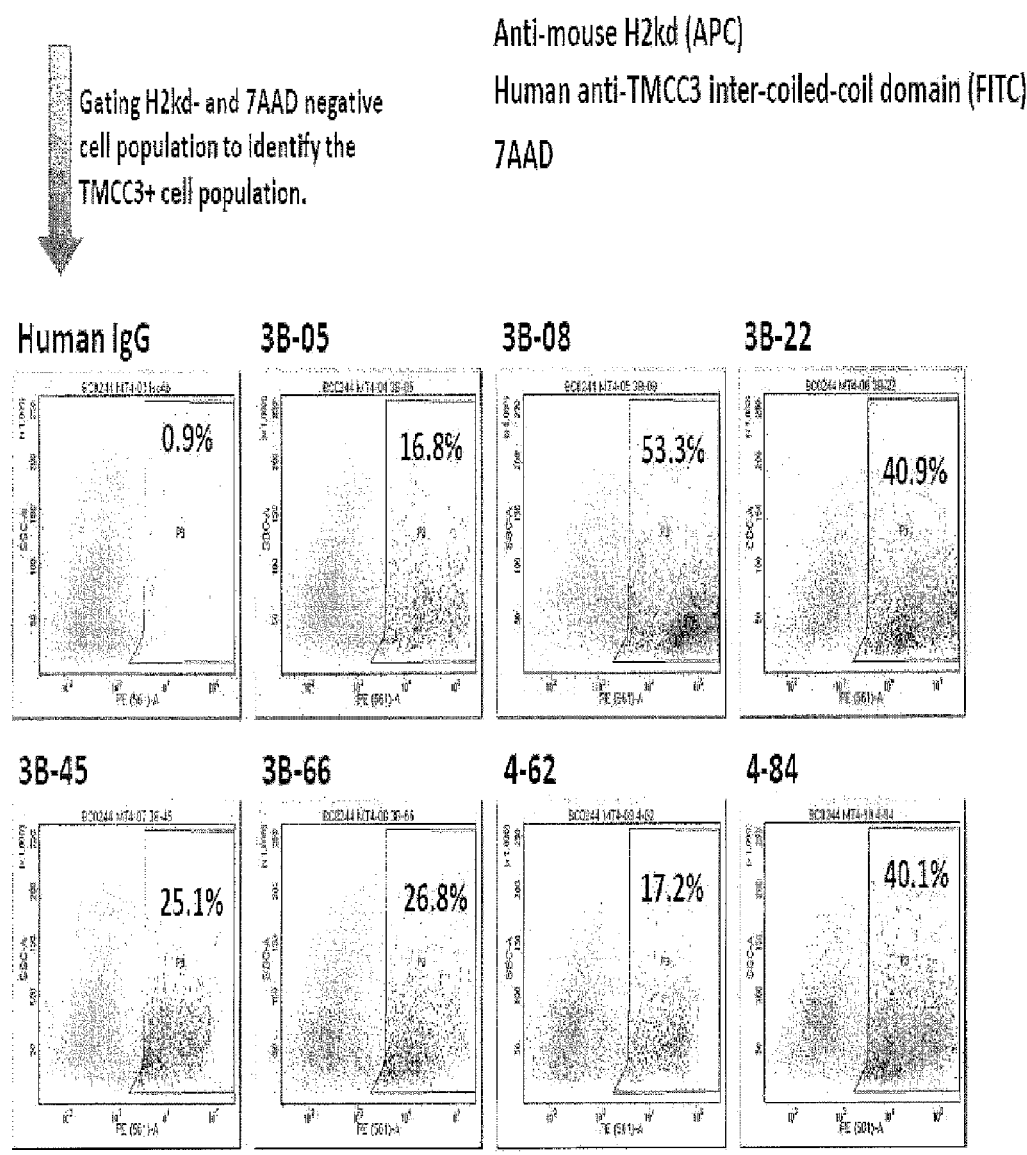
FIG. 23 shows the bindings of various antibodies to a breast cancer xenograph tumor (BC0244). As shown, as compared with the control human IgG, most antibodies of the invention bind strongly to the breast cancer xenograph.
Figure 24:
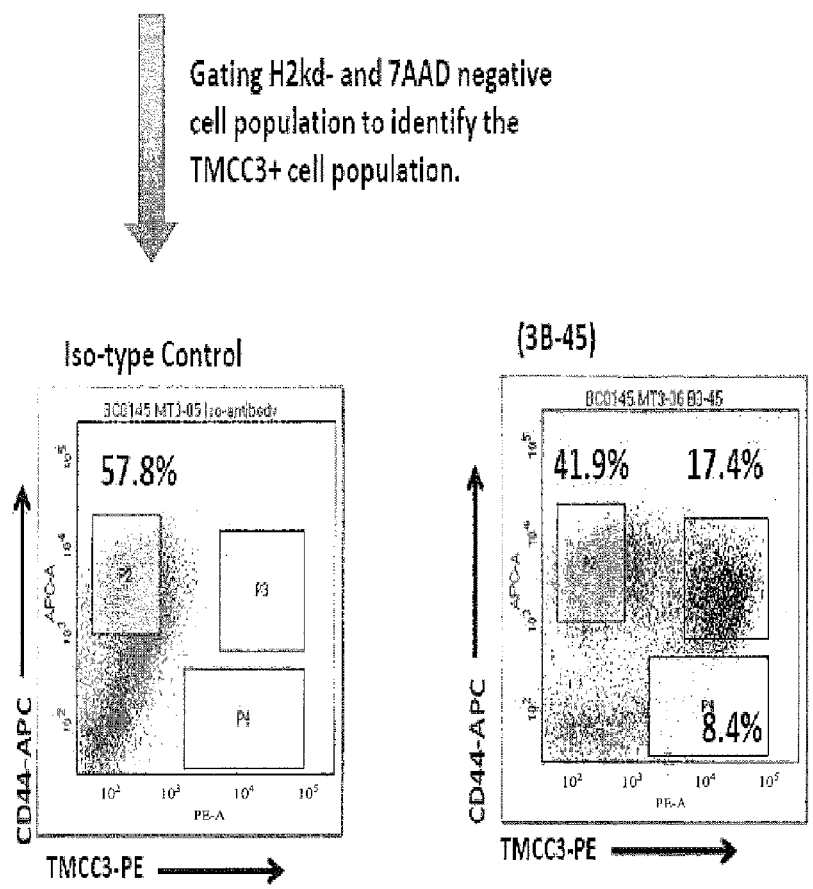
FIG. 24 shows the bindings of 3B-45 antibody to a breast cancer xenograph tumor (BC0145), showing the ability of the antibody to bind with stem cell-like cancer cells.
Figure 25:
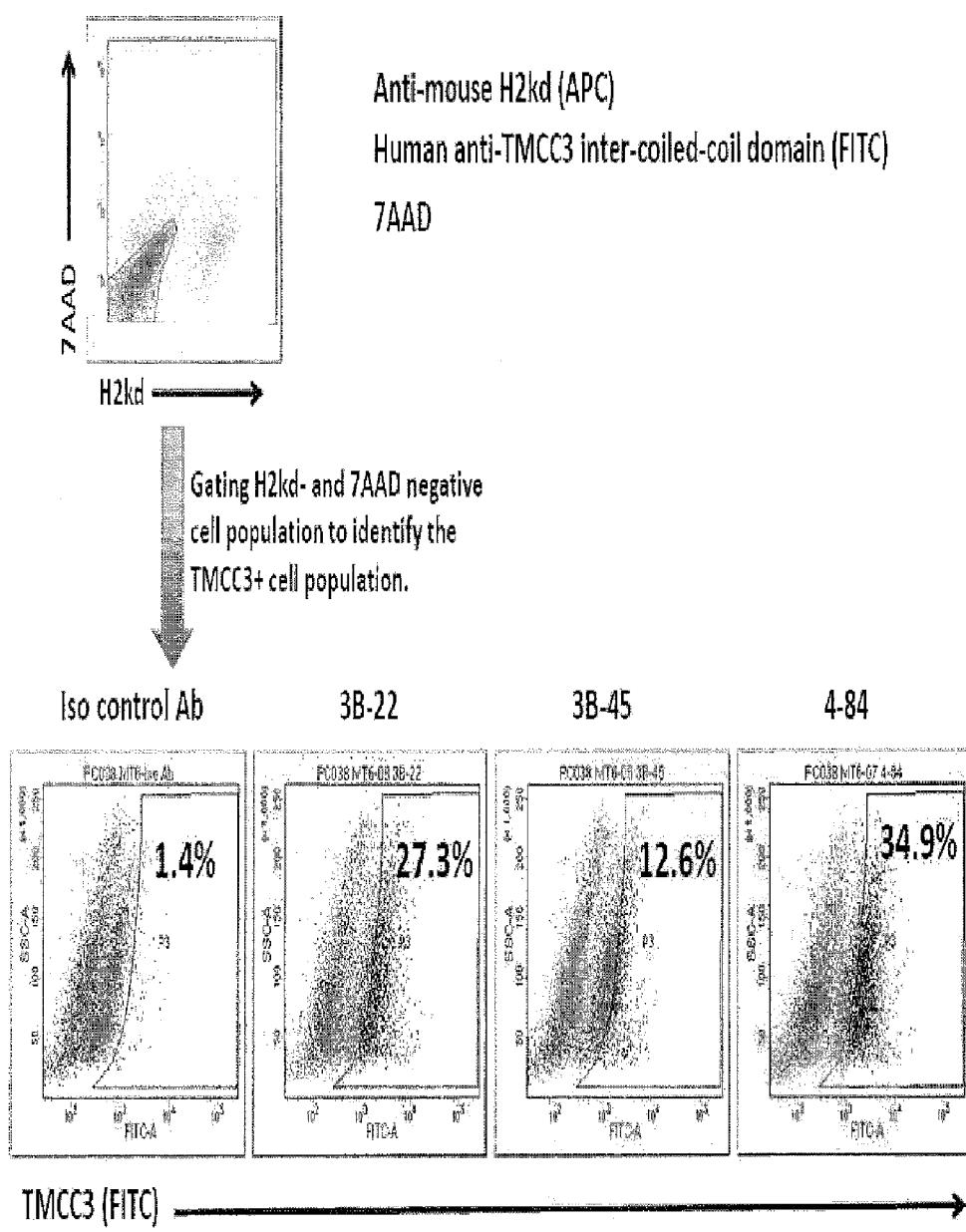
FIG. 25 shows the bindings of 3B-22, 3B-45, and 4-84 antibodies to a pancreatic cancer xenograph tumor (PC038), showing the abilities of these antibodies to bind with subpopulations (presumably the stem cell like cells) of the cancer cells.

In addition to cell lines, these antibodies also bind well to cancer cells in xenographs. FIG. 23 shows the binding of various antibodies of the invention and breast cancer xenograph tumor (BC0244), and FIG. 24 shows similar results with anther breast cancer xenograph tumor (BC0145). In addition to breast cancer xenographs, these antibodies are also effective in binding to pancreatic cancer xenograph (FIG. 25; PC038). Again, these results show that antibodies of the invention can have broad applications in different cancer types.

CDC (Complement Dependent Cytotocixity) Activities of Anti-TMCC3 Antibodies

Figure 26:
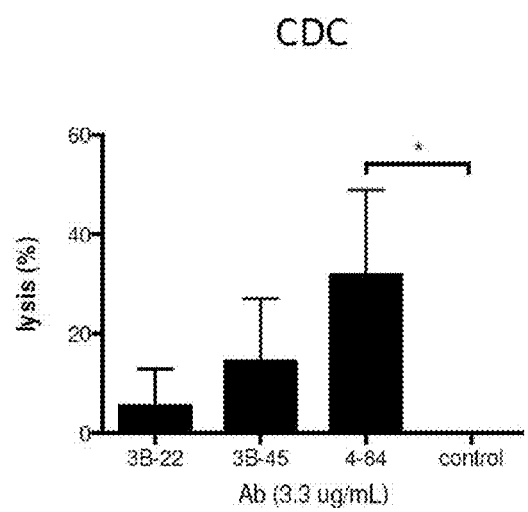
FIG. 26 shows the abilities of the antibodies of the invention to induce CDC (complement dependent cytotoxicity) in breast cancer cell line, MDA MB231. As shown, antibody 4-84 is particularly effective in inducing CDC, resulting in substantial lysis of the target cells.

Antibody binding to a target cell may induce cell killing. This is indeed observed with antibodies of the invention. As shown in FIG. 26, binding of various anti-TMCC3 antibodies to breast cancer cell line MDA-MB231 resulted in complement dependent cytotoxicity. As a result, the breast cancer cells were lyzed. These results indicate that antibodies of the present invention can be effective in binding to cancer cells and inducing lysis of the cancer cells via complement dependent mechanisms. Accordingly, these antibodies would be effective cancer treatment agents.

Figure 27:
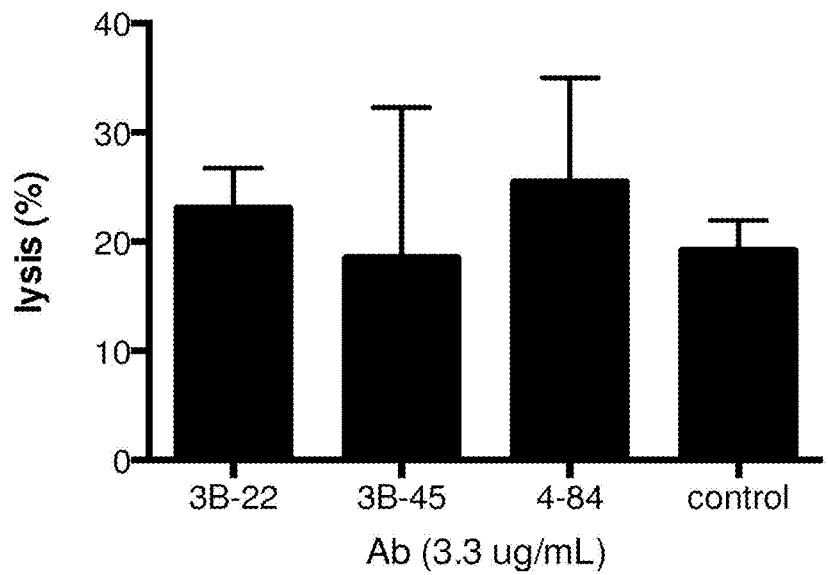
FIG. 27 shows the abilities of the antibodies of the invention to induce ADCC (Antibody-Dependent Cell-Mediated Cytotoxicity) in breast cancer cell line, MDA MB231. Freshly prepared human PBMCs (peripheral blood mononucleated cells) were used as the effector cells and MDA MB231 as the target cells. The ratio of the effector to the target cells is 16.5 in this experiment. The results shown are representative of three independent experiments (three healthy donors). The results show that antibodies 3B-22 and 4-84 are promising in ADCC lysis of the target cancer cells.

Antibody-Dependent Cell-Mediated Cytotoxicity (ADCC) Activities of Anti-TMCC3 Antibodies ADCC is a mechanism of cell-mediated immune defense, by which an effector cell of the immune system can lyse a target cell once the membrane-surface antigens on the target cell are bound by specific antibodies. FIG. 27 shows that antibodies of the invention are also effective in inducing ADCC to lyse the target cancer cells (e.g., MDA MB231). These results indicate that antibodies of the invention can induce target cell lysis via both the CDC and ADCC mechanisms.

Enrichment of Stem Cell-Like Cancer Cells (Also Referred to as "Cancer Stem Cells")

As noted above, the subpopulation of cancer cells that are stem cell like express more TMCC3. These stem cell like cancer cells are more invasive and should be the main focus for cancer therapy managements. To effectively manage and treat these more aggressive cancer cells, one needs a means to identify and isolate these stem cell-like cancer cells.

Figure 28:
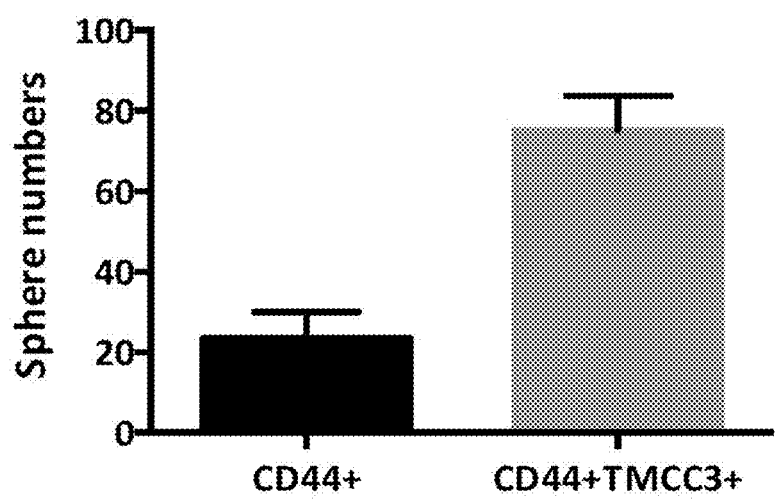
FIG. 28 shows that anti-TMCC3 intercoil domain antibodies can enrich stem cell-like cancer cells. In this experiment, breast cancer cell line BC0145 was used. As shown, the anti-TMCC3 Ab significantly enriched the stem cell-like cancer cell population.

The above antibody binding results indicate that antibodies of the invention would be useful tools for the identification and separation of such stem cell-like cancer cells. FIG. 28 shows one such example—enrichment of stem cell-like cancer cells from BC0145 xenograph.

The fact that these antibodies are effective in enriching the stem cell-like cancer cells indicate that they are useful in both diagnostic and therapy. For diagnostic, they may be used to assess the existence and quantity of stem cell-like cancer cells. The existence of such cells would indicate more invasive cancer types. For therapy applications, these antibodies may be used to target these more invasive population in the cancers, for example by conjugating with a therapeutic agent, a radio isotope, or a cytotoxic agent, or by simply binding to these cells to induce the CDC or ADCC lysis. Alternatively, these antibodies may be used to remove circulating stem cell-like cancer cells. These are limited examples of how these antibodies can be used to diagnose and treat the more aggressive subpopulation of cancer cells. One skilled in the art would appreciate that the applications of these antibodies are not so limited.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims

What is claimed is:

1. A method for treating cancer, comprising: administering to a subject in need thereof an antibody against a transmembrane and coiled-coil domains protein 3 (TMCC3), wherein the antibody binds to an epitope in an extracellular domain of TMCC3, wherein the antibody has a heavy chain and a light chain, wherein the heavy chain having complementary determination regions (CDRs) consisting of CDRH1, CDRH2, and CDRH3, wherein the light chain having CDRs consisting of CDRL1, CDRL2, and CDRL3, wherein CDRH1, CDRH2, and CDRH3 comprise respectively the sequences of SEQ ID NO: 13, SEQ ID NO: 14, and SEQ ID NO: 15, wherein CDRL1, CDRL2, and CDRL3 comprise respectively the sequences of SEQ ID NO: 16, SEQ ID NO: 17, and SEQ ID NO: 18.

2. The method according to claim 1, wherein the antibody binds to an epitope in an intercoil domain of TMCC3.

3. The method according to claim 2, wherein the intercoil domain is located between amino acids 153 and 282 in SEQ ID NO: 1.

4. The method according to claim 1, wherein the cancer is selected from the group consisting of breast cancer, prostate cancer, pancreatic cancer, lung cancer, and hepatoma.

5. The method according to claim 1, wherein the cancer is breast cancer.

6. The method according to claim 5, wherein the antibody binds to an epitope in an intercoil domain of TMCC3.

7. The method according to claim 5, wherein the intercoil domain is located between amino acids 153 and 282 in SEQ ID NO: 1.

* * * * *

SEQUENCE LISTING

<160> NUMBER OF SEQ ID NOS: 19

<210> SEQ ID NO 1
<211> LENGTH: 477
<212> TYPE: PRT
<213> ORGANISM: Homo sapiens

<400> SEQUENCE: 1

```
Met Pro Gly Ser Asp Thr Ala Leu Thr Val Asp Arg Thr Tyr Ser Tyr
1               5                   10                  15

Pro Gly Arg His His Arg Cys Lys Ser Arg Val Glu Arg His Asp Met
                20                  25                  30

Asn Thr Leu Ser Leu Pro Leu Asn Ile Arg Arg Gly Gly Ser Asp Thr
            35                  40                  45

Asn Leu Asn Phe Asp Val Pro Asp Gly Ile Leu Asp Phe His Lys Val
    50                  55                  60

Lys Leu Thr Ala Asp Ser Leu Lys Gln Lys Ile Leu Lys Val Thr Glu
65                  70                  75                  80

Gln Ile Lys Ile Glu Gln Thr Ser Arg Asp Gly Asn Val Ala Glu Tyr
                85                  90                  95

Leu Lys Leu Val Asn Asn Ala Asp Lys Gln Gln Ala Gly Arg Ile Lys
            100                 105                 110

Gln Val Phe Glu Lys Lys Asn Gln Lys Ser Ala His Ser Ile Ala Gln
        115                 120                 125

Leu Gln Lys Lys Leu Glu Gln Tyr His Arg Lys Leu Arg Glu Ile Glu
    130                 135                 140

Gln Asn Gly Ala Ser Arg Ser Lys Asp Ile Ser Lys Asp His Leu
145                 150                 155                 160

Lys Asp Ile His Arg Ser Leu Lys Asp Ala His Val Lys Ser Arg Thr
                165                 170                 175

Ala Pro His Cys Met Glu Ser Ser Lys Ser Gly Met Pro Gly Val Ser
            180                 185                 190

Leu Thr Pro Pro Val Phe Val Phe Asn Lys Ser Arg Glu Phe Ala Asn
        195                 200                 205

Leu Ile Arg Asn Lys Phe Gly Ser Ala Asp Asn Ile Ala His Leu Lys
    210                 215                 220

Asn Ser Leu Glu Glu Phe Arg Pro Glu Ala Ser Ala Arg Ala Tyr Gly
225                 230                 235                 240

Gly Ser Ala Thr Ile Val Asn Lys Pro Lys Tyr Gly Ser Asp Asp Glu
                245                 250                 255

Cys Ser Ser Gly Thr Ser Gly Ser Ala Asp Ser Asn Gly Asn Gln Ser
            260                 265                 270

Phe Gly Ala Gly Gly Ala Ser Thr Leu Asp Ser Gln Gly Lys Leu Ala
        275                 280                 285

Val Ile Leu Glu Glu Leu Arg Glu Ile Lys Asp Thr Gln Ala Gln Leu
    290                 295                 300

Ala Glu Asp Ile Glu Ala Leu Lys Val Gln Phe Lys Arg Glu Tyr Gly
305                 310                 315                 320

Phe Ile Ser Gln Thr Leu Gln Glu Arg Tyr Arg Tyr Glu Arg Leu
                325                 330                 335

Glu Asp Gln Leu His Asp Leu Thr Asp Leu His Gln His Glu Thr Ala
            340                 345                 350

Asn Leu Lys Gln Glu Leu Ala Ser Ile Glu Glu Lys Val Ala Tyr Gln
        355                 360                 365
```

```
Ala Tyr Glu Arg Ser Arg Asp Ile Gln Glu Ala Leu Glu Ser Cys Gln
370                 375                 380

Thr Arg Ile Ser Lys Leu Glu Leu His Gln Gln Glu Gln Gln Ala Leu
385                 390                 395                 400

Gln Thr Asp Thr Val Asn Ala Lys Val Leu Leu Gly Arg Cys Ile Asn
                405                 410                 415

Val Ile Leu Ala Phe Met Thr Val Ile Leu Val Cys Val Ser Thr Ile
                420                 425                 430

Ala Lys Phe Val Ser Pro Met Met Lys Ser Arg Cys His Ile Leu Gly
                435                 440                 445

Thr Phe Phe Ala Val Thr Leu Leu Ala Ile Phe Cys Lys Asn Trp Asp
450                 455                 460

His Ile Leu Cys Ala Ile Glu Arg Met Ile Ile Pro Arg
465                 470                 475

<210> SEQ ID NO 2
<211> LENGTH: 45
<212> TYPE: PRT
<213> ORGANISM: Homo sapiens

<400> SEQUENCE: 2

Val Asn Lys Pro Lys Tyr Gly Ser Asp Asp Glu Cys Ser Ser Gly Thr
1               5                   10                  15

Ser Gly Ser Ala Asp Ser Asn Gly Asn Gln Ser Phe Gly Ala Gly Gly
                20                  25                  30

Ala Ser Thr Leu Asp Ser Gln Gly Lys Leu Ala Val Ile
                35                  40                  45

<210> SEQ ID NO 3
<211> LENGTH: 5867
<212> TYPE: DNA
<213> ORGANISM: Homo sapiens

<400> SEQUENCE: 3
agctgcagca gccgcgccgc ccctcgccc gcggctccca gggtgatccc gagcacagcc      60
ggtggctcgc ggcgcggcag ccccagaaga cgggaaagtt cgcggccgga gcgcggagat     120
gccgggcagc gacacggcgc tcaccgtgga ccggacctac tcggaccccg ccggcaccha    180
ccgctgcaag agccgggtag aacgtcatga catgaatacc ttaagcctgc ccctgaacat     240
acgccgaggg gggtcagaca ccaacctcaa ctttgatgtc ccggatggca tcctggactt     300
ccacaaggtc aaactcactg cagacagcct gaagcaaaaa attctaaagg taacagagca     360
gataaaaatt gagcaaacat cgcgcgatgg gaatgttgcg gagtatctga actagtgaa     420
caacgcagac aagcagcagg cgggacgtat caagcaagtc tttgagaaga gaatcagaa     480
atcagctcac tccatcgccc agctgcagaa gaagttagag cagtatcatc gaaagctcag    540
agagatcgag cagaatggag cctctaggag ctcaaaggac atttccaaag accacctgaa    600
ggatatacat cgctctttga agatgcccca cgtgaaatct cgaactgccc cccattgcat    660
ggagagcagc aaatcgggca tgccaggggt ctcacttact ccacctgtgt tcgttttcaa    720
taagtccaga gagtttgcca acctgatccg gaataagttt ggcagcgccg acaacattgc    780
tcacttgaaa aattccttag aggagtttag gccagaggcg agtgccaggg cctacgggggg   840
cagcgctacc atcgtgaaca aacccaagta tggcagtgat gatgaatgtt cgagtggcac    900
gtcaggctcg gccgacagta acggaaacca gtcgtttggg gctggtggag ccagcacact    960
ggacagccag ggcaagctcg ccgtgatcct ggaggaactg agggagatca aggatacccac   1020
```

```
agctcagctg gctgaggaca tcgaggcact gaaggtgcag tttaagagag aatatggttt   1080
tatttctcag accctgcaag aggaaagata caggtatgag cgactggagg accagctgca   1140
tgacctgacg gacctgcatc agcatgagac agccaacctg aagcaggagc tggccagcat   1200
tgaggagaag gtggcctacc aggcctacga gcgctcgcgg gacatccagg aagccttgga   1260
atcctgccag actcgcattt ctaagctgga gctccaccag caagagcagc aagctctgca   1320
gacagacacc gtgaatgcta aagttctcct ggggaggtgc atcaacgtga tcctggcctt   1380
catgactgtc atcttagtgt gtgtgtccac catcgcgaag ttcgtctcac ccatgatgaa   1440
gagtcgctgc cacattcttg gccttcttc tgccgtgact cttcttgcta tattttgtaa   1500
aaactgggac catatcctgt gtgccataga aaggatgata ataccaagat gaagccactg   1560
gttcctgcct tcaagttctt tcaagttttt attttaaaga aaactctgtg catactacca   1620
aattttacag tgaatgattg tgcggactcg tgtgtaagaa aaactaggac tgtgtggtgt   1680
aaataactac aattctctta actccgtagc agttgccaac tcagtccttg tacttcgtta   1740
acacgaatct gtttcagagc tctcctacct tgctcactgc cttaatcaga ccgatttcct   1800
gcccacctga ccagcccagc gtggtaaacc tctgtatatt gagaccttgg cataattggt   1860
gatcctgaag aaagaggtct ctctcctaag tctctgtcag aattgagctt cacaattgct   1920
aatggttgtt ttctgtgagt cctataaaaa gcaaggatat gcatgattca gggaatgaag   1980
aatcacaggc ttgggcagtg ttaaacactg tggcctatgg tccccgtgtg atccaccctg   2040
cttctctcca ggggaccata ggtcccgtca tgtactcagt gtccacagca gtcagtcgtg   2100
tatgaccctg taacgtggaa atcttatcac acacctgtta tccaacaagt ctacctgagg   2160
ggttttgtta cactttaaat gggaaggcat agggatttat gaatgggct ttcaccttct   2220
catacccagg caaccaacac ctgattttgt ctcaactggc tagcaaatgc ccagccttca   2280
gagtgtgcag gaatgttttc aaatccctca tcagactgtg actttaacat taatttggaa   2340
tcctgtgagc actactctga aggtttgtgt tttggcaaat ctttttttctt ttttgagaca   2400
gggctctgct aaatattgct caggctggtt gcaaactcct tgcttcaagg gatcctccca   2460
cctcagcctc ccaagcagcc gggactgcag gcacaagcca ccatgcctgg ctgtttttg   2520
gcaaatcttg attgtgataa gccccctgg aggatatgat tcactttatg tgattcatct   2580
tattcacagg tctgtgaggg actgcaaagc ttactcagga aatgaaaaca atgatggtc   2640
atgttgcagt ttttccttg aaggacaacc gaaccatagc ctctaaagtt caagtgcact   2700
gaggtgtcgg aacgctgaaa gcatgaggaa acgaggacgt agggtgtgac tgaatggtgg   2760
ctagattagt gggagcagtt cacctggatg aagattgaga gcatcgtctt tgagaagtga   2820
aagactagca agaataaaat aaattaagtc cagtgtttga gccaaggttg ccacctgtct   2880
cttaacatct cactgaacat aagtcctgag gtattaggac gaccatactg cctctgagct   2940
gaaaacattc aaaagttcac atccctgttt ggggatacc attcaccgcc ttcagcccag   3000
atgatacttt cctttaaatc tgtgtctctg tgtgtataac aaagaggaag atggaaacaa   3060
tgttcatgga aactgctgtt gagccccttg tccaccact cccgccatct gctgcaggca   3120
ggaaggcatg tgagtgtacg ttttcttcca ggagacatca ggtcccctg gattcaaatt   3180
aagtgcaata ttttgcaaac agctcttctt agggaaatct cctgaaggaa aaaatgtga   3240
cagaatgttc catagtctga gagaatggaa tcgttgagca tttagtacaa gtccagtgtg   3300
tgtgagcggg acttaggcag ctcaagcttg ctttttttttt taagcgtaca attgagtggt   3360
```

```
tttagtaaat tcacaaactt gttcaaccat caccactatc taattccaga ctcacgcttt      3420
tttaaacaat aaatgtcatt tcatgaaatc tttggtgata aagtattttg gattcagaga      3480
agagctccct taccagtccc accctgatct catggctgtc tctcctttca ttgtcagact      3540 cccccctggtc taccgcgttg atgtgtatac actgatcttt caagtctggg agacagataa     3600
ggaggccagg tgcaaggcag ggaggcagag agaatgttgt gcttccttta gcttttgtat      3660
ttcgatggcc agcattaccc tttacctgtg ggcatcagac tcagcgtggg ctgagtgctg      3720
agtgtaactt acactcctaa atcaagctgg ggcctgggtg ggcccctctt ggtatctgtg      3780
aatctttcca agcaccactt cggacacacc agggattgag tgctgctgtt agtttagaga      3840
aggagagatg tctaaccctt gaggtgaagg gctctgggag ggtccaagaa gacgtaggct      3900
tcattttcac accagcccac accattccag tgctcagcct agcaaatgtg ctttaatgca      3960
cacttctcag acctgtgatc cgtgtatctt ctccccagtg acagaagtag agaagagaat      4020
ggaaagcagc acactccgtc ccctctagtc tggagctgtt aacagaatct gctagaaact      4080
agctttattc taacataccg taggatctaa atcctcctac ctggatcatg aattcctttg      4140
aaataattca tattttcatt gactctcact aaatgtcaaa taaccttgtt ttcacttgga      4200
taggctcaac ctacctggca tatttatttt gcagtcttgt tgaaagttca tgaaactttg      4260 tacttttaa taagatgata cactcgaagg aaacttttaa tctctgcagt ttattctctc       4320
ttaaggaata aacactccca ctgtttgttc tcttcaatgt gtaaggagat taaatgacat      4380
tttagaaata ttacaattaa aaatagtgat gtagctgtaa catatgctgg aattggatat      4440
ttaatttatg tttgtgtcaa ctataatcct ttccccaccc ctttcattta tggtaaacat      4500
cttgggcaaa cccaaagatg gaaagtgctt gttgggtggg taagcaccac ctggtctctc      4560
agcaaacact cctgagtggt tgaagatgct ggacattgga ttctagcact gggtttatct      4620
ggtgacatag tctcctgtgg gtcttgagtt ggttatttca agctcaaact ctgaatatga      4680
ttaaaccaga acaccccacc cccaactgcc aaaaaaaaa aaaaaaatg gaaatccata       4740 atgaaacagc aaaaaagtac tccgttgctg ggtttggaca atgaacatgg gattagtccc      4800
aagtttgtag cttggaacgg tagcattttt gcctgcgtga tccttgtcag ctattcacag      4860
aaggaaatct tccgaaactc cgtctttcat ttcagccggt gaggctgtta tccttctctg      4920
tcaattagca ttcatgtggt tttcgctctt tccagctctg tcactcttgt tttcatttaa      4980
atattgcccc actctgtgtt tattgccttg ccatttctct agcatatcag gtttaattat      5040
gggctcagta ataatgagga actagcttcc ctcaggcaac taattacttt tgtcttttt      5100 ggtcggattg taccaaatta ttttgcattg aatgggaatg ttttgcagt gaatccagat       5160 atagttgtat tggtttggaa aaacatttaa atatatttat tcatatgaac atgtgtgatt      5220
aaacaaccta ttttacatat ttctgtaatt ctgaggagtg ggctgggggt aggaagaaat      5280
ggcaccactt aaaattcagg gcttatatga agaggtgttt taaggttagc acatgcacaa      5340
aggaacgagt tggtttaaaa agataaatca ctgcaaagaa tgaaattggc ttattcacat      5400
caaaactaga taagatgcta aaaaaaaag atatgaaaca gaactaacct atagtttcct       5460
gaaatcagta cagtttaatt tataagaagc tagaaagtaa tgcaccttga ttgttttagg      5520
aatgatttat gtgttgcaat tttaatttat ttaaagcatg tctactgtgt ttgtcctaag      5580
agaaatattt caacaaaacg tgctctgtgt ttaagatatg tttaggcagt agttagcaac      5640
tctgaaagta gaaactggaa atgttttattg tgaggcttgt tgcagaattt ccattttgtg     5700
agttactact tagtttcatg tcagcctaaa attgtaaatt ccctgtagat cttcaccccca     5760
```

```
ttgtggtgtc atcaatgaat ccaaagcagg tgccattatt ttttaaata aacacttgat    5820 gttagctttg gtgttaaata aagaggtaga tttcttaaat tttaaaa               5867

<210> SEQ ID NO 4
<211> LENGTH: 59
<212> TYPE: DNA
<213> ORGANISM: Artificial Sequence
<220> FEATURE:
<223> OTHER INFORMATION: Synthetic

<400> SEQUENCE: 4
ccggcgacaa cattgctcac ttgaactcga gttcaagtga gcaatgttgt cgttttttg        59

<210> SEQ ID NO 5
<211> LENGTH: 59
<212> TYPE: DNA
<213> ORGANISM: Artificial Sequence
<220> FEATURE:
<223> OTHER INFORMATION: Synthetic

<400> SEQUENCE: 5
ccggcgtcat gacatgaata ccttactcga gtaaggtatt catgtcatga cgttttttg        59

<210> SEQ ID NO 6
<211> LENGTH: 59
<212> TYPE: DNA
<213> ORGANISM: Artificial Sequence
<220> FEATURE:
<223> OTHER INFORMATION: Synthetic

<400> SEQUENCE: 6
ccgggatggg aatgttgcgg agtatctcga gatactccgc aacattccca tctttttg         59

<210> SEQ ID NO 7
<211> LENGTH: 31
<212> TYPE: PRT
<213> ORGANISM: Artificial Sequence
<220> FEATURE:
<223> OTHER INFORMATION: Synthetic

<400> SEQUENCE: 7

Pro His Cys Met Glu Ser Ser Lys Ser Gly Met Pro Gly Val Ser Leu
1               5                   10                  15

Thr Pro Pro Val Phe Val Phe Asn Lys Ser Arg Glu Phe Ala Asn
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic

<400> SEQUENCE: 8

Ser Arg Glu Phe Ala Asn Leu Ile Arg Asn Lys Phe Gly Ser Ala Asp
1               5                   10                  15

Asn Ile Ala His Leu Lys Asn Ser Leu Glu Glu Phe Arg Pro Glu
            20                  25                  30

<210> SEQ ID NO 9
<211> LENGTH: 31
<212> TYPE: PRT
<213> ORGANISM: Artificial Sequence
<220> FEATURE:
```

<223> OTHER INFORMATION: Synthetic

<400> SEQUENCE: 9

Glu Glu Phe Arg Pro Glu Ala Ser Ala Arg Ala Tyr Gly Gly Ser Ala
1               5                   10                  15

Thr Ile Val Asn Lys Pro Lys Tyr Gly Ser Asp Asp Glu Cys Ser
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Synthetic

<400> SEQUENCE: 10

Ser Asp Asp Glu Cys Ser Ser Gly Thr Ser Gly Ser Ala Asp Ser Asn
1               5                   10                  15

Gly Asn Gln Ser Phe Gly Ala Gly Gly Ala Ser Thr Leu
            20                  25

<210> SEQ ID NO 11
<211> LENGTH: 67
<212> TYPE: PRT
<213> ORGANISM: Artificial Sequence
<220> FEATURE:
<223> OTHER INFORMATION: Synthetic

<400> SEQUENCE: 11

Asp Ile Ser Lys Asp His Leu Lys Asp Ile His Arg Ser Leu Lys Asp
1               5                   10                  15

Ala His Val Lys Ser Arg Thr Ala Pro His Cys Met Glu Ser Ser Lys
            20                  25                  30

Ser Gly Met Pro Gly Val Ser Leu Thr Pro Pro Val Phe Val Phe Asn
        35                  40                  45

Lys Ser Arg Glu Phe Ala Asn Leu Ile Arg Asn Lys Phe Gly Ser Ala
    50                  55                  60

Asp Asn Ile
65

<210> SEQ ID NO 12
<211> LENGTH: 66
<212> TYPE: PRT
<213> ORGANISM: Artificial Sequence
<220> FEATURE:
<223> OTHER INFORMATION: Synthetic

<400> SEQUENCE: 12

Gly Ser Ala Asn Ile Ala His Leu Lys Asn Ser Leu Glu Glu Phe Arg
1               5                   10                  15

Pro Glu Ala Ser Ala Arg Ala Tyr Gly Gly Ser Ala Thr Ile Val Asn
            20                  25                  30

Lys Pro Lys Arg Gly Ser Asp Asp Glu Cys Ser Ser Gly Thr Ser Gly
        35                  40                  45

Ser Ala Asp Ser Asn Gly Asn Gln Ser Phe Gly Ala Gly Gly Ala Ser
    50                  55                  60

Thr Leu
65

<210> SEQ ID NO 13
<211> LENGTH: 10

-continued

```
<212> TYPE: PRT
<213> ORGANISM: Mus musculus

<400> SEQUENCE: 13

Gly Phe Asn Ile Lys Asp Tyr Tyr Met His
1               5                   10

<210> SEQ ID NO 14
<211> LENGTH: 17
<212> TYPE: PRT
<213> ORGANISM: Mus musculus

<400> SEQUENCE: 14

Trp Ile Asp Pro Glu Asn Gly Asp Thr Glu Tyr Ala Pro Lys Phe Asp
1               5                   10                  15
Gly

<210> SEQ ID NO 15
<211> LENGTH: 4
<212> TYPE: PRT
<213> ORGANISM: Mus musculus

<400> SEQUENCE: 15

Asn Phe Asp Tyr
1

<210> SEQ ID NO 16
<211> LENGTH: 10
<212> TYPE: PRT
<213> ORGANISM: Mus musculus

<400> SEQUENCE: 16

Ser Ala Ser Ser Ser Val Ser Tyr Met Tyr
1               5                   10

<210> SEQ ID NO 17
<211> LENGTH: 7
<212> TYPE: PRT
<213> ORGANISM: Mus musculus

<400> SEQUENCE: 17

Asp Thr Ser Asn Leu Ala Ser
1               5

<210> SEQ ID NO 18
<211> LENGTH: 9
<212> TYPE: PRT
<213> ORGANISM: Mus musculus

<400> SEQUENCE: 18

Gln Gln Tyr Ser Gly Tyr Pro Leu Thr
1               5

<210> SEQ ID NO 19
<211> LENGTH: 30
<212> TYPE: PRT
<213> ORGANISM: Artificial Sequence
<220> FEATURE:
<223> OTHER INFORMATION: Synthetic

<400> SEQUENCE: 19

Asp Ile Ser Lys Asp His Leu Lys Asp Ile His Arg Ser Leu Lys Asp
1               5                   10                  15
```

-continued

```
Ala His Val Lys Ser Arg Thr Ala Pro His Cys Met Glu Ser
            20                  25                  30
```